United States Patent
Diaz et al.

(10) Patent No.: US 7,829,588 B2
(45) Date of Patent: Nov. 9, 2010

(54) MODULATORS OF THE PPAR-TYPE RECEPTORS AND PHARMACEUTICAL/COSMETIC APPLICATIONS THEREOF

(75) Inventors: Philippe Diaz, Nice (FR); Catherine Raffin, Antibes (FR)

(73) Assignee: Galderma Research & Development, Biot (FR)

( * ) Notice: Subject to any disclaimer, the term of this patent is extended or adjusted under 35 U.S.C. 154(b) by 1012 days.

(21) Appl. No.: 11/450,392

(22) Filed: Jun. 12, 2006

(65) Prior Publication Data

US 2007/0054907 A1    Mar. 8, 2007

Related U.S. Application Data

(63) Continuation of application No. PCT/EP2004/014810, filed on Dec. 8, 2004.

(60) Provisional application No. 60/530,234, filed on Dec. 18, 2003.

(30) Foreign Application Priority Data

Dec. 11, 2003   (FR) .................................... 03 14535

(51) Int. Cl.
*A61K 31/41*    (2006.01)
*C07D 249/00*   (2006.01)
(52) U.S. Cl. ................... 514/383; 548/262.2
(58) Field of Classification Search ................ 514/383; 548/262.2
See application file for complete search history.

(56) References Cited

U.S. PATENT DOCUMENTS

2005/0187275 A1*   8/2005   Quattropani et al. ........ 514/383

FOREIGN PATENT DOCUMENTS

WO      WO 98/32444 A1      7/1998
WO      WO 03/018553 A1     3/2003

OTHER PUBLICATIONS

Rivier et al., J. Invest. Dermatol., 111, 1998, p. 116-1121, esp. p. 1120.*

* cited by examiner

*Primary Examiner*—Susannah Chung
(74) *Attorney, Agent, or Firm*—Buchanan Ingersoll & Rooney PC

(57) ABSTRACT

Novel compounds that are modulators of PPAR-type receptors having the structural formula (I):

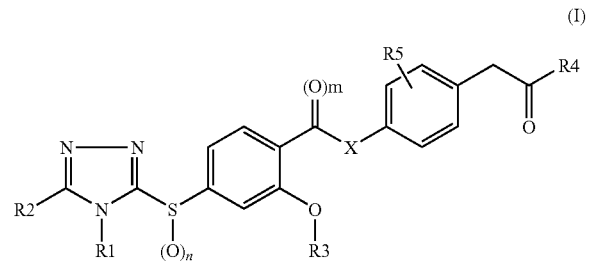

are formulated into pharmaceutical compositions suited for administration in human or veterinary medicine (in dermatology, and in the field of cardiovascular diseases, immune diseases and/or diseases linked to the metabolism of lipids), or, alternatively, into cosmetic compositions.

17 Claims, 2 Drawing Sheets

MODULATORS OF THE PPAR-TYPE RECEPTORS AND PHARMACEUTICAL/COSMETIC APPLICATIONS THEREOF

CROSS-REFERENCE TO PRIORITY/PCT/PROVISIONAL APPLICATIONS

This application claims priority under 35 U.S.C. §119 of FR 03/14535, filed Dec. 11, 2003, and of Provisional Application No. 60/530,234, filed Dec. 18, 2003, and is a continuation of PCT/EP 2004/014810 filed Dec. 8, 2004 and designating the United States, published in the English language as WO 2005/058844 A2 on Jun. 30, 2005, each hereby expressly incorporated by reference and each assigned to the assignee hereof.

BACKGROUND OF THE INVENTION

1. Technical Field of the Invention

The present invention relates, as novel and useful industrial products, to a novel class of compounds which are modulators of the Peroxisome Proliferator-Activated Receptor (PPAR) type receptors. This invention also relates to their method of preparation and to their formulation into pharmaceutical compositions for administration in human or veterinary medicine, or, alternatively, into cosmetic compositions.

2. Description of Background and/or Related and/or Prior Art

The activity of the PPAR-type receptors has been the subject of numerous studies. There may be mentioned, as a guide, the publication entitled "Differential Expression of Peroxisome Proliferator-Activated Receptor Subtypes During the Differentiation of Human Keratinocytes", Michel Rivier et al., *J. Invest. Dermatol.*, 111, 1998, p. 1116-1121, in which a large number of bibliographic references relating to PPAR-type receptors is listed. There may also be mentioned, as a guide, the dossier entitled "The PPARs: From Orphan Receptors to Drug Discovery", Timothy M. Willson, Peter J. Brown, Daniel D. Sternbach, and Brad R. Henke, *J. Med. Chem.*, 2000, Vol. 43, p. 527-550.

The PPAR receptors activate transcription by binding to elements of DNA sequences, called peroxisome proliferator response elements (PPRE), in the form of a heterodimer with the retinoid X receptors (called RXRs).

Three human PPAR subtypes have been identified and described: PPARα, PPARγ and PPARδ (or NUC1). PPARα is mainly expressed in the liver while PPARδ is ubiquitous.

It is described in WO 98/32444 that PPARα selective compounds play a role in the barrier function and the differentiation of the stratum corneum.

PPARγ is the most widely studied of the three subtypes. All the references suggest a critical role of the PPARγ receptors in the regulation of differentiation of adipocytes, where it is highly expressed. It also plays a key role in systemic lipid homeostasis.

It has in particular been described in WO 96/33724 that PPARγ-selective compounds, such as prostaglandin-J2 or -D2, are potential active agents for treating obesity and diabetes.

SUMMARY OF THE INVENTION

The present invention provides a novel class of PPAR-modulating compounds.

Thus, the present invention features compounds corresponding to the following general formula (I):

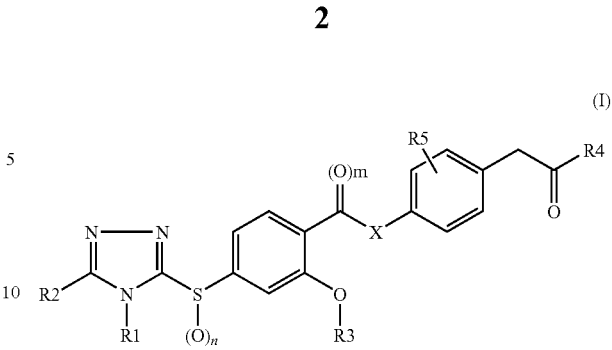

in which:

R$_1$ is a hydrogen atom, an alkyl radical, an aryl or heteroaryl radical, or an aralkyl radical;

R$_2$ is a hydrogen atom, an alkyl radical optionally substituted with an aryl radical or with a heteroaryl radical, a radical —CH$_2$OR$_6$, or an aryl radical;

R$_6$ is as defined below;

X is —S—, —Se—, —O— or —N—R$_7$;

R$_7$ is as defined below;

R$_3$ is an alkyl radical or an aralkyl radical;

R$_4$ is a hydroxyl radical, an alkoxyl radical or the radical —N(R$_8$, R$_9$);

R$_8$ and R$_9$ are as defined below;

R$_5$ is a hydrogen atom, a halogen atom, an alkyl radical, an alkoxyl radical or a hydroxyl radical;

R$_6$ is an aryl radical or a heteroaryl radical;

R$_7$ is a hydrogen atom, an alkyl radical, an aralkyl radical, or a radical —C(Y)R$_{10}$;

R$_{10}$ is as defined below;

R$_8$ and R$_9$, which may be identical or different, are each a hydrogen atom, an alkyl radical, or together form, with the nitrogen atom from which they depend, a morpholino, piperidino or pyrrolidino group;

R$_{10}$ is a hydrogen atom, an alkyl radical, an alkoxyl radical, or a radical —NR$_{11}$;

R$_{11}$ is as defined below;

R$_{11}$ is a hydrogen atom, an alkyl radical or an aralkyl radical;

Y is an oxygen or a sulfur atom;

n is an integer ranging from 0 to 2;

m is 0 or 1;

and when X is S or Se and m is 0, then n is 0, and the optical and/or geometric isomers, which are pure or in the form of a mixture, in any proportions, of the said compounds of formula (I), the tautomeric and N-oxide forms, and the salts of the said compounds of formula (I).

For the compounds of formula (I) which is presented below, the term "geometric isomer" means a cis/trans or E/Z isomer. More particularly, the possible double bond(s) present in the various substituents of the compounds of general formula (I) may be of the E or Z configuration. These geometric isomers, which are pure or not, alone or in the form of a mixture, form an integral part of the compounds of formula (I).

The term "optical isomer" groups together all the isomer forms, which are alone or in the form of mixtures, due to the presence of one or more axes and/or centers of symmetry in the molecule, and leading to the rotation of a beam of polarized light. The term "optical isomer" comprises more particularly the enantiomers and the diastereoisomers, in pure form or in the form of a mixture.

The acids which are capable of forming pharmaceutically acceptable salts with the compounds of formula (I) above are organic or inorganic acids. By way of non-limiting examples, there may be mentioned hydrochloric, hydrobromic, phosphoric, sulfuric, tartaric, citric, maleic, acetic, fumaric, alkylsulfonic, naphthalenesulfonic, para-toluenesulfonic, bistrifluoroacetic and camphoric acids.

The bases which are capable of forming pharmaceutically acceptable salts with the compounds of formula (I) above are inorganic or organic bases. Among these bases, there may be mentioned, by way of non-limiting examples, alkali or alkaline-earth metal hydroxides, for example sodium or potassium hydroxide, but also ammonia, diethylamine, triethylamine, ethanolamine, diethanolamine, piperidine, piperazine, morpholine, basic amino acids such as arginine and lysine, osamines, for example meglumine and amino alcohols such as 3-aminobutanol and 2-aminobutanol.

In particular, when the compounds according to the invention exist in the form of salts, they are salts of an alkali or alkaline-earth metal, zinc salts or salts of an organic amine.

The present invention comprehends in particular the pharmaceutically acceptable salts, as indicated above, but also the salts allowing appropriate separation or crystallization of the compounds of formula (I), such as the salts obtained with chiral amines.

The compounds of formula (I) above also comprise the prodrugs of these compounds. The expression "prodrugs" is understood to mean compounds which, once administered to the patient, are chemically and/or biologically converted by the living organism to compounds of formula (I).

In particular, when the compounds according to the invention exist in the form of salts, they are salts of an alkali or alkaline-earth metal, zinc salts or salts of an organic amine.

Figure 1:
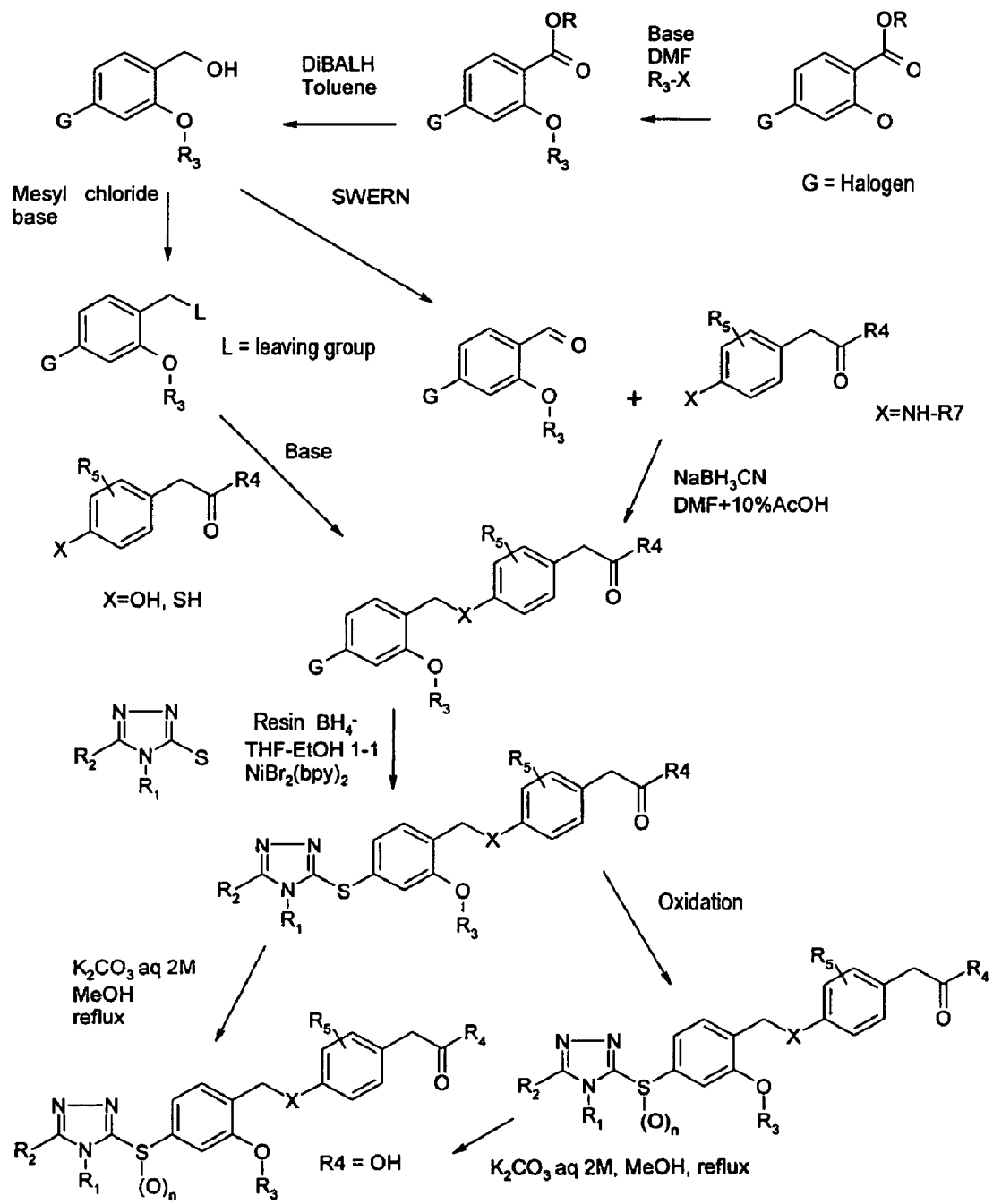
FIGS. 1 and 2 illustrate certain reaction schemes for preparing the compounds of formula (I).

DETAILED DESCRIPTION OF BEST MODE AND SPECIFIC/PREFERRED EMBODIMENTS OF THE INVENTION

According to the present invention, the expression hydroxyl radical means the —OH radical.

According to the present invention, the expression alkyl radical means a linear or cyclic, optionally branched and optionally fluorinated or perfluorinated radical containing 1 to 12 carbon atoms.

Preferably, the alkyl radicals having from 1 to 12 carbon atoms are methyl, ethyl, n-propyl, isopropyl, n-butyl, isobutyl, tert-butyl, n-pentyl, hexyl, octyl, decyl, dodecyl or cyclohexyl radicals.

The expression alkoxyl radical means a radical having from 1 to 7 carbon atoms, such as methoxyl, ethoxyl, isopropyloxyl, tert-butoxyl, hexyloxyl, benzyloxyl or phenoxyl radicals, each being optionally substituted with one (or more) alkyl radicals.

The expression aryl radical means a phenyl, biphenyl or naphthyl radical, optionally fused with one or more other rings and optionally mono- or di-substituted with one or more atoms, groups, functional groups or radicals selected from a halogen atom, a $CF_3$ radical, an alkyl radical, an alkoxyl radical, a nitro functional group.

The expression aralkyl radical means a benzyl, phenethyl or naphthylen-2-ylmethyl radical which is optionally mono- or disubstituted with one or more atoms, groups, functional groups or radicals selected from a halogen atom, a $CF_3$ radical, an alkyl radical, an alkoxyl radical, a nitro functional group, an alkyl ester group, a carboxyl functional group, a hydroxyl radical, an amino functional group which is optionally substituted with at least one alkyl radical.

The expression heteroaryl radical means an aryl radical which is interrupted by one or more heteroatoms O, N, S, Se, such as the pyridyl, furyl, thienyl, isoxazolyl, oxadiazolyl, oxazolyl, imidazolyl, isothiazolyl, quinazolinyl, benzothiadiazolyl, benzimidazolyl, indolyl or benzofuryl radical, optionally substituted with one or more atoms, groups, functional groups or radicals selected from a halogen atom, a $CF_3$ radical, an alkyl radical, an alkoxyl radical, a nitro functional group, an alkyl ester group, a carboxyl functional group, a hydroxyl radical, an amino functional group which is optionally substituted with at least one alkyl radical.

According to the present invention, the compounds of formula (I) which are more particularly preferred are those for which at least one, and preferably all the conditions below are satisfied:

X is a nitrogen atom,
R1 is an alkyl radical or an aryl radical,
R2 is a hydrogen atom, an alkyl radical, an aryl radical,
R7 is a hydrogen atom or an alkyl radical,
m is equal to 0,
n is equal to 0, and the possible optical and/or geometric isomers, which are pure or in the form of a mixture, in any proportions, of these compounds, and their possible tautomeric and N-oxide forms, and salts of the said compounds.

Among the compounds of formula (I) above according to the present invention, the following compounds are particularly exemplary (alone or in the form of a mixture):

1. Ethyl(4-{4-[5-(4-tert-butylphenyl)-4-methyl-4H-[1,2,4]-triazol-3-ylsulfanyl]-2-heptyloxybenzylamino}phenyl)acetate;
2. (4-{4-[5-(4-tert-Butylphenyl)-4-methyl-4H-[1,2,4]-triazol-3-ylsulfanyl]-2-heptyloxybenzylamino}phenyl)acetic acid;
3a. (4-{4-[5-(4-tert-Butylphenyl)-4-methyl-4H-[1,2,4]-triazol-3-ylsulfanyl]-2-phenethyloxybenzylamino}phenyl)acetic acid;
3b. Ethyl(4-{4-[5-(4-tert-butylphenyl)-4-methyl-4H-[1,2,4]-triazol-3-ylsulfanyl]-2-phenethyloxybenzylamino}phenyl)acetate;
4a. (4-{4-[5-(4-tert-Butylphenyl)-4-methyl-4H-[1,2,4]-triazol-3-ylsulfanyl]-2-benzyloxybenzylamino}phenyl)acetic acid;
4b. Ethyl(4-{4-[5-(4-tert-butylphenyl)-4-methyl-4H-[1,2,4]-triazol-3-ylsulfanyl]-2-benzyloxybenzylamino}phenyl)acetate;
5a. (4-{4-[5-(4-tert-Butylphenyl)-4-methyl-4H-[1,2,4]-triazol-3-ylsulfanyl]-2-propoxybenzylamino}phenyl)acetic acid;
5b. Ethyl(4-{4-[5-(4-tert-butylphenyl)-4-methyl-4H-[1,2,4]-triazol-3-ylsulfanyl]-2-propoxybenzylamino}phenyl)acetate;
6a. {4-[4-(4-Methyl-4H-[1,2,4]-triazol-3-ylsulfanyl)-2-heptyloxybenzylamino]phenyl}acetic acid;
6b. Ethyl {4-[4-(4-methyl-4H-[1,2,4]-triazol-3-ylsulfanyl)-2-heptyloxybenzylamino]phenyl}acetate;
7a. {4-[4-(4-Methyl-4H-[1,2,4]-triazol-3-ylsulfanyl)-2-phenethyloxybenzylamino]phenyl}acetic acid;

7b. Ethyl {4-[4-(4-methyl-4H-[1,2,4]-triazol-3-ylsulfanyl)-2-phenethyloxybenzyl amino]phenyl}acetate;

8a. {4-[4-(4-Methyl-4H-[1,2,4]-triazol-3-ylsulfanyl)-2-benzyloxybenzylamino]phenyl}acetic acid;

8b. Ethyl {4-[4-(4-methyl-4H-[1,2,4]-triazol-3-ylsulfanyl)-2-benzyloxybenzylamino]phenyl}acetate;

9a. {4-[4-(4-Methyl-4H-[1,2,4]-triazol-3-ylsulfanyl)-2-propoxybenzylamino]phenyl}acetic acid;

9b. Ethyl {4-[4-(4-methyl-4H-[1,2,4]-triazol-3-ylsulfanyl)-2-propoxybenzylamino]phenyl}acetate;

10a. (4-{4-[5-(4,5-Dichloroimidazol-1-ylmethyl)-4-methyl-4H-[1,2,4]-triazol-3-ylsulfanyl]-2-heptyloxybenzylamino}phenyl)acetic acid;

10b. Ethyl(4-{4-[5-(4,5-dichloroimidazol-1-ylmethyl)-4-methyl-4H-[1,2,4]-triazol-3-ylsulfanyl]-2-heptyloxybenzylamino}phenyl)acetate;

11a. (4-{4-[5-(4,5-Dichloroimidazol-1-ylmethyl)-4-methyl-4H-[1,2,4]-triazol-3-ylsulfanyl]-2-phenethyloxybenzylamino}phenyl)acetic acid;

11b. Ethyl(4-{4-[5-(4,5-dichloroimidazol-1-ylmethyl)-4-methyl-4H-[1,2,4]-triazol-3-ylsulfanyl]-2-phenethyloxybenzylamino}phenyl)acetate;

12a. (4-{4-[5-(4,5-Dichloroimidazol-1-ylmethyl)-4-methyl-4H-[1,2,4]-triazol-3-ylsulfanyl]-2-benzyloxybenzylamino}phenyl)acetic acid;

12b. Ethyl(4-{4-[5-(4,5-dichloroimidazol-1-ylmethyl)-4-methyl-4H-[1,2,4]-triazol-3-ylsulfanyl]-2-benzyloxybenzylamino}phenyl)acetate;

13a. (4-{4-[5-(4-tert-Butylphenyl)-4-(4-chlorophenyl)-4H-[1,2,4]-triazol-3-ylsulfanyl]-2-benzyloxy benzylamino}phenyl)acetic acid;

13b. Ethyl(4-{4-[5-(4-tert-butylphenyl)-4-(4-chlorophenyl)-4H-[1,2,4]-triazol-3-ylsulfanyl]-2-benzyloxy benzylamino}phenyl)acetate;

14a. (4-{4-[5-(4-tert-Butylphenyl)-4-(4-chlorophenyl)-4H-[1,2,4]-triazol-3-ylsulfanyl]-2-phenethyloxy benzylamino}phenyl)acetic acid;

14b. Ethyl(4-{4-[5-(4-tert-butylphenyl)-4-(4-chlorophenyl)-4H-[1,2,4]-triazol-3-ylsulfanyl]-2-phenethyloxy benzylamino}phenyl)acetate;

15a. (4-{4-[5-(4-tert-Butylphenyl)-4-(4-chlorophenyl)-4H-[1,2,4]-triazol-3-ylsulfanyl]-2-propoxy benzylamino}phenyl)acetic acid;

15b. Ethyl(4-{4-[5-(4-tert-butylphenyl)-4-(4-chloro phenyl)-4H-[1,2,4]-triazol-3-ylsulfanyl]-2-propoxy benzylamino}phenyl)acetate;

16a. {4-[4-(4-Methyl-5-thiophen-3-ylmethyl-4H-[1,2,4]-triazol-3-ylsulfanyl)-2-heptyloxylbenzylamino]phenyl}acetic acid;

16b. Ethyl {4-[4-(4-methyl-5-thiophen-3-ylmethyl-4H-[1,2,4]-triazol-3-ylsulfanyl)-2-heptyloxy benzylamino]phenyl}acetate;

17a. {4-[4-(4-Methyl-5-thiophen-3-ylmethyl-4H-[1,2,4]-triazol-3-ylsulfanyl)-2-benzyloxybenzylamino]phenyl}acetic acid;

17b. Ethyl {4-[4-(4-methyl-5-thiophen-3-ylmethyl-4H-[1,2,4]-triazol-3-ylsulfanyl)-2-benzyloxybenzyl amino]phenyl}acetate;

18a. {4-[4-(4-Methyl-5-thiophen-3-ylmethyl-4H-[1,2,4]-triazol-3-ylsulfanyl)-2-phenethyloxybenzylamino]phenyl}acetic acid;

18b. Ethyl {4-[4-(4-methyl-5-thiophen-3-ylmethyl-4H-[1,2,4]-triazol-3-ylsulfanyl)-2-phenethyloxybenzyl amino]phenyl}acetate;

19a. {4-[4-(4-Methyl-5-thiophen-3-ylmethyl-4H-[1,2,4]-triazol-3-ylsulfanyl)-2-propoxybenzylamino]phenyl}acetic acid;

19b. Ethyl {4-[4-(4-methyl-5-thiophen-3-ylmethyl-4H-[1,2,4]-triazol-3-ylsulfanyl)-2-propoxybenzylamino]phenyl}acetate;

20a. (4-{4-[5-(7-Methylindan-4-yloxymethyl)-4-phenyl-4H-[1,2,4]-triazol-3-ylsulfanyl]-2-heptyloxybenzyl amino}phenyl)acetic acid;

20b. Ethyl(4-{4-[5-(7-methylindan-4-yloxymethyl)-4-phenyl-4H-[1,2,4]-triazol-3-ylsulfanyl]-2-heptyloxybenzyl amino}phenyl)acetate;

21a. (4-{4-[5-(7-Methylindan-4-yloxymethyl)-4-phenyl-4H-[1,2,4]-triazol-3-ylsulfanyl]-2-benzyloxybenzyl amino}phenyl)acetic acid;

21b. Ethyl(4-{4-[5-(7-methylindan-4-yloxymethyl)-4-phenyl-4H-[1,2,4]-triazol-3-ylsulfanyl]-2-benzyloxybenzyl amino}phenyl)acetate;

22a. (4-{4-[5-(7-Methylindan-4-yloxymethyl)-4-phenyl-4H-[1,2,4]-triazol-3-ylsulfanyl]-2-phenethyloxybenzyl amino}phenyl)acetic acid;

22b. Ethyl(4-{4-[5-(7-methylindan-4-yloxymethyl)-4-phenyl-4H-[1,2,4]-triazol-3-ylsulfanyl]-2-phenethyloxyben zyl amino}phenyl)acetate;

23a. (4-{4-[5-(7-Methylindan-4-yloxymethyl)-4-phenyl-4H-[1,2,4]-triazol-3-ylsulfanyl]-2-propoxybenzyl amino}phenyl)acetic acid;

23b. Ethyl(4-{4-[5-(7-methylindan-4-yloxymethyl)-4-phenyl-4H-[1,2,4]-triazol-3-ylsulfanyl]-2-propoxybenzyl amino}phenyl)acetate;

24. Methyl(4-{4-[5-(4-tert-butylphenyl)-4-methyl-4H-[1,2,4]-triazol-3-ylsulfanyl]-2-heptyloxybenzylamino}phenyl)acetate;

25. 2-(4-{4-[5-(4-tert-Butylphenyl)-4-methyl-4H-[1,2,4]-triazol-3-ylsulfanyl]-2-heptyloxybenzylamino}phenyl)-N-hexylacetamide;

26. 2-(4-{4-[5-(4-tert-Butylphenyl)-4-methyl-4H-[1,2,4]-triazol-3-ylsulfanyl]-2-heptyloxy benzylamino}phenyl)-1-morpholin-4-ylethanone;

27. 2-(4-{4-[5-(4-tert-Butylphenyl)-4-methyl-4H-[1,2,4]-triazol-3-ylsulfanyl]-2-heptyloxybenzylamino}phenylacetamide;

28. 2-(4-{4-[5-(4-tert-Butylphenyl)-4-methyl-4H-[1,2,4]-triazol-3-ylsulfanyl]-2-heptyloxybenzylamino}phenyl)-N-ethylacetamide;

29. {4-[4-(5-Heptyl-4-methyl-4H-[1,2,4]-triazol-3-ylsulfanyl)-2-heptyloxybenzyloxy]phenyl}acetic acid methyl ester;

30. {4-[2-Heptyloxy-4-(5-hexyl-4-methyl-4H-[1,2,4]-triazol-3-ylsulfanyl)benzyloxy]phenyl}acetic acid;

31. {4-[4-(5-Heptyl-4-methyl-4H-[1,2,4]-triazol-3-ylsulfanyl)-2-propoxybenzylamino]phenyl}acetic acid ethyl ester;

32. 4-[2-Propoxy-4-(5-pyridin-4-yl-4H-[1,2,4]-triazol-3-ylsulfanyl)benzylamino]phenyl}acetic acid ethyl ester;

33. {4-[4-(4-Methyl-5-pyridin-4-yl-4H-[1,2,4]-triazol-3-ylsulfanyl)-2-propoxybenzylamino]phenyl}acetic acid ethyl ester;

34. {4-[4-(5-Heptyl-4-methyl-4H-[1,2,4]-triazol-3-ylsulfanyl)-2-propoxybenzylamino]phenyl}acetic acid;

35. {4-[2-Propoxy-4-(5-pyridin-4-yl-4H-[1,2,4]-triazol-3-ylsulfanyl)benzylamino]phenyl}acetic acid;

36. {4-[4-(4-Methyl-5-pyridin-4-yl-4H-[1,2,4]-triazol-3-ylsulfanyl)-2-propoxybenzylamino]phenyl}acetic acid;

37. Butyl(4-{4-[5-(4-tert-butylphenyl)-4-methyl-4H-[1,2,4]-triazol-3-ylsulfanyl]-2-heptyloxybenzyl amino}phenyl)acetate;

38. Octyl(4-{4-[5-(4-tert-butylphenyl)-4-methyl-4H-[1,2,4]-triazol-3-ylsulfanyl]-2-heptyloxybenzyl amino}phenyl)acetate;

39. Nonyl(4-{4-[5-(4-tert-butylphenyl)-4-methyl-4H-[1,2,4]-triazol-3-ylsulfanyl)-2-heptyloxybenzyl amino}phenyl)acetate;
40. 2-(4-{4-[5-(4-tert-Butylphenyl)-4-methyl-4H-[1,2,4]-triazol-3-ylsulfanyl)-2-heptyloxybenzyl amino}phenyl)-N-methylacetamide;
41. 2-(4-{4-[5-(4-tert-Butylphenyl)-4-methyl-4H-[1,2,4]-triazol-3-ylsulfanyl)-2-heptyloxybenzyl amino}phenyl)-N-ethylacetamide;
42. 2-(4-{4-[5-(4-tert-Butylphenyl)-4-methyl-4H-[1,2,4]-triazol-3-ylsulfanyl)-2-heptyloxybenzyl amino}phenyl)-N-pentylacetamide;
43. 2-(4-{4-[5-(4-tert-Butylphenyl)-4-methyl-4H-[1,2,4]-triazol-3-ylsulfanyl)-2-heptyloxybenzyl amino}phenyl)-N-heptylacetamide;
44. (4-{4-[5-(4-tert-Butylphenyl)-4-methyl-4H-[1,2,4]-triazol-3-ylsulfanyl)-2-heptyloxybenzyloxy}phenyl)acetic acid;
45. Methyl(4-{4-[5-(4-tert-butylphenyl)-4-methyl-4H-[1,2,4]-triazol-3-ylsulfanyl)-2-heptyloxybenzyl oxy}phenyl)acetate;
46. Methyl(4-{4-[5-(4-tert-butylphenyl)-4-methyl-4H-[1,2,4]-triazol-3-ylsulfanyl)-2-heptyloxybenzyl sulfanyl}phenyl)acetate;
47. (4-{4-[5-(4-tert-Butylphenyl)-4-methyl-4H-[1,2,4]-triazol-3-ylsulfanyl)-2-heptyloxybenzyl sulfanyl}phenyl)acetic acid; and
48. 2-(4-{4-[5-(4-tert-Butylphenyl)-4-methyl-4H-[1,2,4]-triazol-3-ylsulfanyl]-2-heptyloxybenzylamino}phenyl)-N-octylacetamide.

Figure 2:
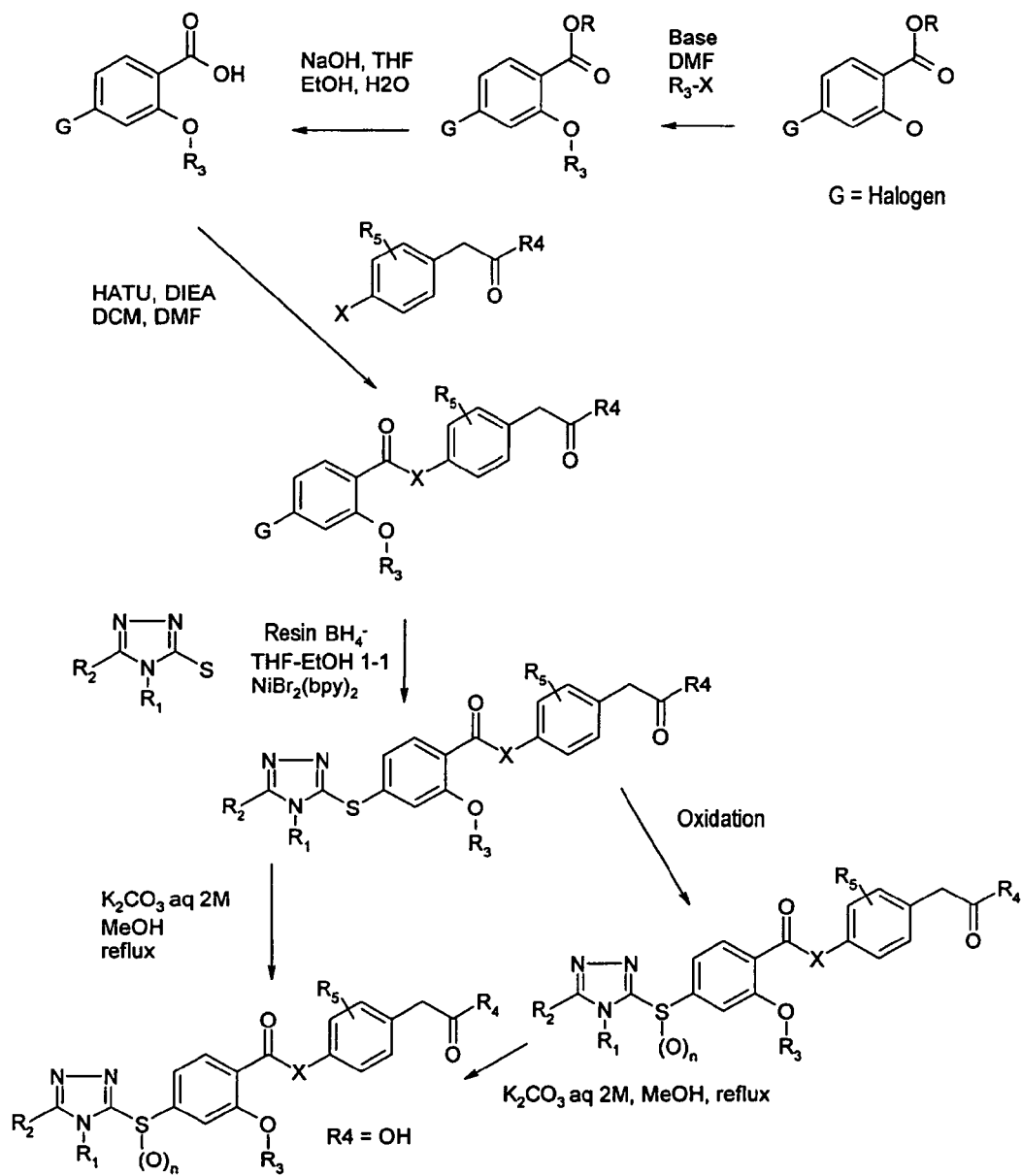

The reaction scheme described in FIGS. 1 and 2 is a general scheme allowing the production of the compounds according to the invention.

The compounds of general formula (I) may be obtained (FIGS. 1 and 2) by alkylation of the hydroxyl group of an ester of salicylic acid, halogenated at the para position with respect to the ester group COOR, in the presence of a base, such as potassium or caesium carbonate, and of an alkyl halide such as iodoheptane in an aprotic polar solvent (Step 1). The ester is then obtained and subjected to the various steps below based on one of the three routes detailed below:

Route A in the Case where m=0 and X=NR$_7$:

The ester obtained during Step 1 is then reduced to an aldehyde, for example by the succession of a reduction with a metal hydride such as diisobutylaluminum hydride followed by an oxidation, for example by a Swern reaction. The next step is a reductive amination with the aid of an aromatic amine with the aldehyde previously obtained, which may be carried out with the isolation of the intermediate imine or not, and then reduction of the latter by the action of a reducing agent such as sodium cyanoborohydride (NaBH$_3$CN). The haloarylamine obtained may then be subjected to coupling with a thiol, by virtue of the use of a metal catalyst such as nickel, palladium or copper derivatives, optionally in the presence of a hydride donor such as sodium borohydride, supported or not, and if necessary of a base. The sulfur atom of the derivatives obtained is then optionally oxidized to a sulfone or sulfoxide, and then optionally hydrolysed to give the corresponding acids.

Route B in the Case where m=0 and X=0, S, Se:

The ester obtained during Step 1 is then reduced to an alcohol, for example with the aid of a metal hydride such as diisobutylaluminum hydride. The alcohol obtained is then converted to a leaving group by the action of a base and of a reagent such as tosyl or mesyl chloride. By the reaction of an alcohol, of a thiol or of a selenized derivative in the presence of a base such as potassium carbonate and/or optionally of a reducing agent such as sodium borohydride, supported or not, the corresponding ether, thioether or selenoether is obtained. As in Route A, the derivative thus obtained may then be subjected to coupling with a thiol, by virtue of the use of a metal catalyst such as nickel, palladium or copper derivatives, optionally in the presence of a hydride donor such as sodium borohydride, supported or not, and if necessary of a base. The sulfur atom of the derivatives obtained is then optionally oxidized to a sulfone or a sulfoxide, and then optionally hydrolysed to give the corresponding acids.

Route C in the Case where m=1:

The ester obtained during Step 1 is then saponified to give the corresponding acid and then reacted with an aromatic alcohol, an aromatic thiol or an aromatic amine to give the corresponding ester, thioester or amide. As in Route A, the derivative thus obtained may then be subjected to coupling with a thiol, by virtue of the use of a metal catalyst such as nickel, palladium or copper derivatives, optionally in the presence of a hydride donor such as sodium borohydride, supported or not, and if necessary of a base. The sulfur atom of the esters or imides obtained is then optionally oxidized to a sulfone or a sulfoxide. The derivatives, which may or may not be oxidized, are then optionally hydrolysed to give the corresponding acids.

Those skilled in the art will be capable of adapting the operating conditions described above according to the various substituents present in the compounds of formula (I). Thus, the synthesis scheme presented in FIGS. 1 and 2 should be considered as an example of a possible route of synthesis, variants to this route of synthesis being also possible and easily accessible to those skilled in the art.

The starting compounds are either known or are easily prepared by syntheses of which the procedures are either known to the art, or are available and easily accessible in the patent and non-patent literature, and in "Chemical Abstracts", online databases and the internet.

The compounds according to the invention have PPAR-type receptor modulating properties. This activity on the PPARα, δ and γ receptors is measured in a transactivation test and quantified by the dissociation constant Kdapp (apparent), as described in Example 25.

The preferred compounds of the present invention have a dissociation constant of less than or equal to 1 000 nM, and advantageously of less than or equal to 500 nM for at least one of the PPAR subtypes.

The present invention also features, as medicaments, the compounds of formula (I) as described above.

The present invention also features formulation of the compounds of formula (I) into compositions suited for regulating and/or restoring the metabolism of skin lipids.

The compounds according to the invention are particularly suitable in the fields of the following treatments:

for treating dermatological complaints, conditions or afflictions linked to a keratinization disorder related to cell differentiation and proliferation, in particular to treat acne vulgaris, comedo-type acne, polymorphic acne, acne rosacea, nodulocystic acne, acne conglobata, senile acne, secondary acne such as solar acne, acne medicamentosa or occupational acne;

for treating other types of keratinization disorders, in particular ichthyosis, ichthyosiform states, Darrier's disease, keratosis palmaris et plantaris, leukoplasia and leukoplasiform states, cutaneous or mucosal (buccal) lichen;

for treating other dermatological complaints, conditions or afflictions with an inflammatory immunoallergic component, with or without cell proliferation disorder, and in particular all the forms of psoriasis, whether cutaneous, mucosal or ungual, and even psoriatic rheumatism, or cutaneous atopy, such as eczema or respiratory atopy or gingival hypertrophy;

for treating any dermal or epidermal proliferations whether benign or malignant, whether of viral origin or not, such as verruca vulgaris, verruca plana and epidermodysplasia verruciformis, oral or florid papillomatoses, T lymphoma, and proliferations which may be induced by ultraviolet radiation, in particular in the case of baso- and spinocellular epitheliomas, and any precancerous skin lesions such as keratoacanthomas;

for treating other dermatological disorders such as immune dermatoses such as lupus erythematosus, bullous immune diseases and collagen diseases, such as scleroderma;

in the treatment of dermatological or general complaints, conditions or afflictions with an immunological component;

in the treatment of skin disorders due to exposure to UV radiation and for repairing or combating skin aging, whether photoinduced or chronological or for reducing actinic keratoses and pigmentations, or any pathologies associated with chronological or actinic aging, such as xerosis;

for combating sebaceous function disorders such as acne hyperseborrhoea, simple seborrhoea, or seborrhoeic dermatitis;

for preventing or treating cicatrization disorders, or for preventing or repairing stretch marks;

in the treatment of pigmentation disorders, such as hyperpigmentation, melasma, hypopigmentation or vitiligo;

in the treatment of lipid metabolism complaints, conditions or afflictions, such as obesity, hyperlipidaemia, non-insulin-dependent diabetes or X syndrome;

in the treatment of inflammatory complaints, conditions or afflictions such as arthritis;

in the treatment or prevention of cancerous or precancerous states;

in the prevention or treatment of alopecia of different origins, in particular alopecia due to chemotherapy or to radiation;

in the treatment of immune system disorders, such as asthma, diabetes mellitus type I, multiple sclerosis, or other selective dysfunctions of the immune system; and in the treatment of complaints, conditions or afflictions of the cardiovascular system such as arteriosclerosis or hypertension.

The present invention also features cosmetic or pharmaceutical compositions comprising, formulated into a physiologically acceptable medium, at least one compound of formula (I) as defined above.

The administration of the compositions according to the invention, whether regime or regimen, may be carried out orally, parenterally, topically or ocularly. Preferably, the pharmaceutical composition is packaged in a form suitable for application by the topical route.

By the oral route, the composition, more particularly the pharmaceutical composition, may be provided in the form of tablets, gelatin capsules, sugar-coated tablets, syrups, suspensions, solutions, powders, granules, emulsions, lipid or polymeric microspheres or nanospheres or vesicles allowing controlled release. By the parenteral route, the composition may be provided in the form of solutions or suspensions for perfusion or injection.

The compounds according to the invention are generally administered in a regime or regimen at a daily dose of about 0.001 mg/kg to 100 mg/kg of body weight, in 1 to 3 doses.

The compounds are administered by the systemic route at a concentration generally of from 0.001% to 10% by weight, preferably from 0.01% to 1% by weight, relative to the weight of the composition.

By the topical route, the pharmaceutical composition according to the invention is more particularly suited for the treatment of the skin and the mucous membranes and may be provided in the form of salves, creams, milks, ointments, powders, impregnated pads, syndets, solutions, gels, sprays, mousses, suspensions, lotions, sticks, shampoos or washing bases. It may also be provided in the form of suspensions of lipid or polymeric microspheres or nanospheres or vesicles or of polymeric patches and of hydrogels allowing controlled release. This composition for the topical route may be provided in anhydrous form, in aqueous form or in the form of an emulsion.

The compounds are administered by the topical route at a concentration which is generally from 0.001% to 10% by weight, preferably from 0.01% to 1% by weight, relative to the total weight of the composition.

The compounds of formula (I) according to the invention also find application in the cosmetics field, in particular in body and hair care, and more particularly for regulating and/or restoring skin lipid metabolism.

This invention therefore also features the cosmetic use of a composition comprising, formulated into a physiologically acceptable carrier, at least one of the compounds of formula (I) for body or hair care.

The cosmetic compositions according to the invention containing, in a cosmetically acceptable carrier, at least one compound of formula (I) or one of its optical or geometric isomers or one of its salts, may be provided in particular in the form of a cream, a milk, a lotion, a gel, suspensions of lipid or polymeric microspheres or nanospheres or vesicles, impregnated pads, solutions, sprays, mousses, sticks, soaps, shampoos or washing bases.

The concentration of compound of formula (I) in the cosmetic compositions preferably ranges from 0.001% to 3% by weight, relative to the total weight of the composition.

The pharmaceutical and cosmetic compositions as described above may in addition contain inert additives, or even pharmacodynamically active additives as regards the pharmaceutical compositions, or combinations of these additives, and in particular:

wetting agents;
flavor enhancers;
preservatives such as esters of parahydroxybenzoic acid;
stabilizers;
moisture regulators;
pH regulators;
osmotic pressure modifiers;
emulsifiers;
UV-A and UV-B screening agents;
anti-oxidants, such as $\alpha$-tocopherol, butylated hydroxyanisole or butylated hydroxytoluene, Super Oxide Dismutase, Ubiquinol or certain metal chelators;
depigmenting agents such as hydroquinone, azelaic acid, caffeic acid or kojic acid;
emollients;
moisturizing agents such as glycerol, PEG 400, thiamorpholinone and its derivatives, or urea;
anti-seborrhoeic or anti-acne agents, such as S-carboxymethylcysteine, S-benzylcysteamine, their salts or their derivatives, or benzoyl peroxide;

antibiotics such as erythromycin and its esters, neomycin, clindamycin and its esters, tetracyclines;

anti-fungal agents such as ketoconazole or 4,5-polymethylene-3-isothiazolidones;

agents promoting hair regrowth, such as Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine 2,4-dione);

non-steroidal anti-inflammatory agents;

carotenoids and, in particular, β-carotene;

anti-psoriatic agents such as anthralin and its derivatives;

5,8,11,14-eicosatetraynoic and 5,8,11-eicosatriynoic acids, their esters and amides;

retinoids, that is to say ligands for the RAR or RXR receptors, which may be natural or synthetic;

corticosteroids or oestrogens;

α-hydroxy acids and α-keto acids or their derivatives, such as lactic, malic, citric, glycolic, mandelic, tartaric, glyceric and ascorbic acids, and their salts, amides or esters, or β-hydroxy acids or their derivatives, such as salicylic acid and its salts, amides or esters;

ion channel, such as potassium channel, blockers;

or, alternatively, more particularly for pharmaceutical compositions, in combination with medicaments known to interfere with the immune system (for example cyclosporine, FK 506, glucocorticoids, monoclonal antibodies, cytokines or growth factors, and the like).

Of course, one skilled in this art will be careful to choose the possible compound(s) to be added to these compositions such that the advantageous properties intrinsically associated with the present invention are not or not substantially impaired by the addition envisaged.

Several examples of production of active compounds of formula (I) according to the invention, results of biological activity thereof and various specific formulations based on such compounds, will now be given by way of illustration, it being understood that same are only illustrative and in nowise limitative. In said examples to follow, all parts and percentages are given by weight, unless otherwise indicated.

EXAMPLES

The products were analyzed by HPLC/Mass. Column: 2.1×5 mm, 3μ, High purity C18 Hypersil.

Mobile phase: A (CH$_3$CN/0.1 v/v HCO$_2$H); B (H$_2$O/0.1 v/v HCO$_2$H),

Waters Alliance 2790 LC Mobile Phase

| Solvents | A % | 35.0 Solvent A |
| | B % | 65.0 Solvent B |
| Flow rate (ml/min) | | 0.450 |
| Analytical time (min) | | 5.00 |
| Column temperature (° C.) | | 60 |
| Maximum column temperature (° C.) | | 10 |
| Waters Alliance 2790 LC Rapid Equilibration System time (min) | | 0.30 |
| Re-equilibration time (min) | | 0.50 |

The gradient contains 3 entries which are:

| Time | A % | B % | Flow rate | Curve |
|------|-----|-----|-----------|-------|
| 0.00 | 35.0 | 65.0 | 0.450 | 1 |
| 3.00 | 95.0 | 5.0 | 0.450 | 6 |
| 5.00 | 95.0 | 5.0 | 0.450 | 6 |

Example 1

Synthesis of Ethyl(4-{4-[5-(4-tert-butylphenyl)-4-methyl-4H-[1,2,4]-triazol-3-ylsulfanyl]-2-heptyloxybenzylamino}phenyl)acetate Step a: Methyl 2-heptyloxy-4-iodobenzoate A mixture of methyl 2-hydroxy-4-iodobenzoate (25 g, 90 mmol), caesium carbonate (35.2 g, 108 mmol) and n-heptyl iodide (19.2 ml, 117 mmol), in 500 ml of dimethylformamide (DMF) is stirred for 10 hours at room temperature. The solution is neutralized by addition of 2N hydrochloric acid solution. The desired product is extracted by addition of ethyl acetate. The organic phase is washed with water, dried with magnesium sulfate and concentrated using a rotary evaporator. After evaporation of the solvent, 33.84 g (100%) of the expected compound are recovered in the form of a brown oil.

Step b: Preparation of (2-Heptyloxy-4-iodophenyl)methanol

A 1M solution of DiBAlH (87.5 ml, 87.5 mmol) is added dropwise to a solution of methyl 2-heptyloxy-4-iodobenzoate obtained in Step a (14 g, 43.7 mmol) in toluene (450 ml), at 0° C. After stirring for 2 hours, a saturated solution of mixed tartrate of sodium and of potassium is added and then the desired product is extracted by addition of ethyl ether. The organic phase is washed with water, dried with magnesium sulfate and concentrated using a rotary evaporator. The product is purified by chromatography on a silica column, eluted with a heptane/ethyl acetate 9:1 mixture. After evaporation of the solvents, 13.64 g (90%) of the expected compound are recovered in the form of a yellow oil.

Step c: Preparation of 2-Heptyloxy-4-iodobenzaldehyde

A solution of dimethyl sulfoxide (DMSO) (41.4 mmol, 3 ml) in dichloromethane (10 ml) is added to a solution of 1.8 ml of oxalyl chloride (20.7 mmol) in 55 ml of dichloromethane, dropwise, at −78° C. After stirring for 15 minutes, a solution of (2-heptyloxy-4-iodophenyl)methanol obtained in Step b (6.55 g, 18.8 mmol) in 25 ml of dichloromethane is added dropwise. After stirring for 20 minutes, 14 ml of triethylamine are added. After stirring for 2 hours, the reaction medium is hydrolysed by addition of water. The desired product is extracted by addition of ethyl acetate. The organic phase is washed with water, dried with magnesium sulfate and concentrated using a rotary evaporator. After evaporation of the solvents, 6.49 g (100%) of the expected compound are recovered in the form of a yellow solid.

Step d: Preparation of Ethyl [4-(2-heptyloxy-4-iodobenzylamino)phenyl]acetate A solution of ethyl(4-aminophenyl)acetate (1.76 g, 9.84 mmol) and acetic acid (0.71 ml) in DMF (71 ml) is added to a solution of 2-heptyloxy-4-iodobenzaldehyde of Step c (3.1 g, 8.94 mmol), acetic acid (0.71 ml) in DMF (71 ml). The mixture is stirred for 12 hours and then 1.12 g of sodium cyanoborohydride (17.89 mmol) is added. The mixture is heated at 60° C. for 4 hours. The desired product is extracted by addition of ethyl ether. The organic phase is washed with brine and then with water, dried with magnesium sulfate and concentrated using a rotary evaporator. The product is purified by chromatography on a silica column, eluted with a heptane/ethyl acetate 9:1 mixture. After evaporation of the solvents, 4.11 g (96%) of the expected compound are recovered in the form of a yellow oil.

$^1$H NMR/CDCl$_3$: 0.9 (t, 3H); 1.2 to 1.4 (m, 7H); 1.5 (m, 2H); 1.8 (m, 2H); 3.5 (s, 2H); 4 (t, 2H); 4.1 (q, 2H); 4.3 (s, 2H); 6.6 (d, 2H); 7 (d, 1H); 7.1 (dd, 2H); 7.2 (d, 1H); 7.25 (d, 1H); 7.3 (s, 1H).

Step e: Synthesis of Ethyl(4-{4-[5-(4-tert-butylphenyl)-4-methyl-4H-[1,2,4]-triazol-3-ylsulfanyl]-2-heptyloxybenzyl amino}phenyl)acetate A solution of ethyl [4-(2-heptyloxy-4-iodo benzylamino) phenyl]acetate obtained in Step d (4.11 g, 8.07 mmol) in a mixture of tetrahydrofuran (THF) (18 ml) and ethanol (18 ml) is added dropwise to a mixture of 5-(4-tert-butylphenyl)-4-methyl-4H-[1,2,4]-triazole-3-thiol (2.99 g, 12.1 mmol), bis (bipyridine)nickel (II) bromide (106 mg, 0.2 mmol) (*Organometallics*, 4, (1985), 657-661) and 9.68 g of borohydride polymer supported on Amberlite® IRA400 resin at 2.5 mmol/g (Aldrich) in 18 ml of a mixture of THF and ethanol 50:50. The mixture is heated for 20 hours under reflux, and then filtered at room temperature. The filtrate is concentrated using a rotary evaporator. The product is purified by chromatography on a silica column, eluted with a heptane/ethyl acetate 7:3 mixture. After evaporation of the solvents, 4.58 g (90%) of the expected compound are recovered in the form of an oil.

$^1$H NMR/CDCl$_3$: 0.9 (t, 3H); 1.25 to 1.3 (m, 7H); 1.4 (s, 9H); 1.5 (m, 2H); 1.8 (m, 2H); 3.5 (s, 2H); 3.6 (s, 3H); 4 (t, 2H); 4.1 (q, 2H); 4.3 (s, 2H); 6.6 (d, 2H); 6.9 (d, 1H); 7 (s, 1H); 7.1 (d, 2H); 7.3 (d, 1H); 7.5 (d, 2H); 7.6 (d, 2H).

HPLC/Mass Analysis:

Column: Waters Atlantis: dC18, 150×2.1 mm, 3 8iµm, eluent A: acetonitrile+formic acid 0.1%; eluent B: water+formic acid 0.1%, Gradient: 0 min 90% B, 0-25 min: 90 to 5% B, flow rate: 0.5 ml/min, detection: UV, Mass: positive electrospray

| | |
|---|---|
| → HPLC (% total of the surface area): | 99.5 |
| → Mass spectrometry (ES) (M+H⁺): | 629 |

Example 2

Synthesis of (4-{4-[5-(4-tert-Butylphenyl)-4-methyl-4H-[1,2,4]-triazol-3-ylsulfanyl]-2-heptyloxybenzylamino}phenyl)acetic acid A solution of ethyl(4-{4-[5-(4-tert-butylphenyl)-4-methyl-4H-[1,2,4]-triazol-3-yl sulfanyl]-2-heptyloxybenzylamino}phenyl)acetate obtained in Example 1 (2.5 g, 4 mmol) of a 2M aqueous potassium carbonate solution (32 ml) in methanol (65 ml) is heated under reflux for 3 hours. The organic phase is acidified at room temperature with a 2N hydrochloric acid solution to pH 5. The desired product is extracted by addition of ethyl acetate. The organic phase is washed with water, dried with magnesium sulfate and concentrated using a rotary evaporator. The product is purified by chromatography on a silica column, eluted with a heptane/ethyl acetate 4:6 mixture. After evaporation of the solvents, 1.7 g (70%) of the expected compound are recovered in the form of a yellow amorphous solid.

Melting point (m.p.): 71° C.

$^1$H NMR/DMSO$_{d6}$: 0.9 (t, 3H); 1.25 to 1.3 (m, 4H); 1.3 (s, 9H); 1.4 (m, 2H); 1.7 (m, 2H); 3.7 (s, 3H); 4 (t, 2H); 4.2 (d, 2H); 6 (m, 1H); 6.4 (d, 2H); 6.8 (d, 1H); 6.9 (d, 2H); 7 (s, 1H); 7.2 (d, 2H); 7.6 (d, 2H); 7.7 (d, 2H).

The compound of Example 2 may also be obtained by parallel chemistry, according to the procedure described for the following compounds 2 to 23.

Examples 2 to 23

Synthesis of Compounds 2 to 23

Compounds 2 to 23 were obtained by parallel chemistry. The reactions for coupling for a triazole-thiol with a previous iodinated starting compound obtained by reductive amination of FMOC-(4-amino phenyl)acetic acid grafted on Mimotope Lanterns are carried out in several reactors simultaneously following the procedure described below.

Alkylation of the Phenols:

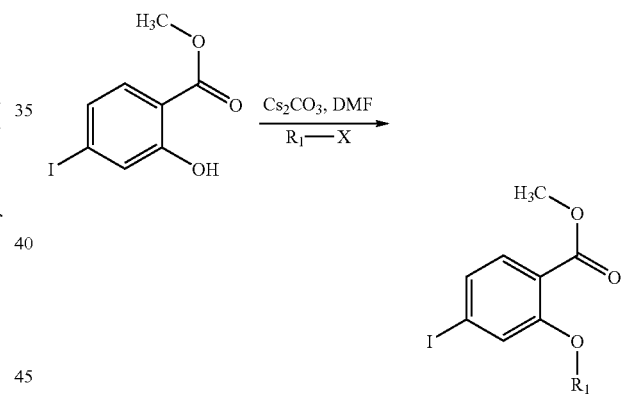

Methyl 2-heptyloxy-4-iodobenzoate

A suspension of caesium carbonate (35.2 g, 108 mmol), methyl 4-iodo-2-hydroxybenzoate (25 g, 90 mmol), iodoheptane (19.2 ml, 117 mmol) in DMF (500 ml) is stirred for 10 hours at room temperature. The organic phase is acidified at room temperature with a 2N hydrochloric acid solution to pH 5. The desired product is extracted by addition of ethyl acetate. The organic phase is washed with water, dried with magnesium sulfate and concentrated using a rotary evaporator. After evaporation of the remainder of the iodoheptane by placing the oil obtained under vacuum produced by a rotary vane pump, 33.8 g (100%) of the expected compound are recovered in the form of a brown oil.

Methyl 4-iodo-2-propoxybenzoate

The procedure is the same as that followed above using 10.6 ml of bromoheptane. The suspension is stirred for 24 hours at room temperature. The organic phase is acidified at room temperature with a 2N hydrochloric acid solution to pH 5. The desired product is extracted by addition of ethyl ether. The organic phase is washed with water, dried with magnesium sulfate and concentrated using a rotary evaporator. 28.2 g (98%) of the expected compound are recovered in the form of a brown oil. The product is purified by chromatography on a silica column, eluted with a heptane/ethyl acetate 9.5:0.5 mixture. After evaporation of the solvents, 25.9 g (75%) of the expected compound are recovered in the form of a yellow oil.

Methyl 4-iodo-2-phenethyloxybenzoate

A suspension of caesium carbonate (35.2 g, 108 mmol), methyl 4-iodo-2-hydroxybenzoate (25 g, 90 mmol), phenethyl bromide (16 ml, 117 mmol) in DMF (500 ml) is stirred for 10 hours at room temperature. Caesium carbonate (20 g, 61.4 mmol) and phenethyl bromide (8.5 ml, 61.4 mmol) are added to the suspension. The organic phase is acidified at room temperature with a 2N hydrochloric acid solution to pH 5. The desired product is extracted by addition of ethyl ether. The organic phase is washed with water, dried with magnesium sulfate and concentrated using a rotary evaporator.

Methyl 2-benzyloxy-4-iodobenzoate

The procedure is the same as that followed for methyl 4-iodo-2-phenethyloxybenzoate, using 5.6 ml of benzyl bromide, 14 g of caesium carbonate and 10 g of methyl 4-iodo-2-hydroxybenzoate in 200 ml of DMF. The suspension is stirred for 48 hours at room temperature. The organic phase is acidified at room temperature with a 2N hydrochloric acid solution to pH 5. The desired product is extracted by addition of ethyl ether. The organic phase is washed with water, dried with magnesium sulfate and concentrated using a rotary evaporator. 14 g of the expected compound are recovered in the form of a brown solid.

Reduction of the Esters:

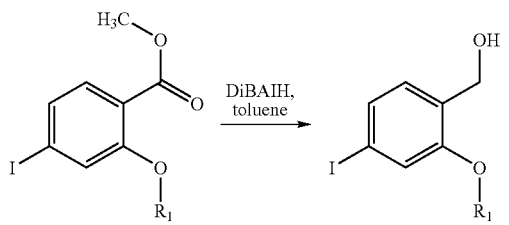

(2-Heptyloxy-4-iodophenyl)methanol 87.5 ml of a solution of diisobutylaluminum hydride (DiBAlH) is added at 0° C. to a solution of methyl 2-heptyloxy-4-iodobenzene (14 g, 43.7 mmol) previously obtained, in toluene (450 ml). The solution is stirred for 2 hours at 0° C., and then a saturated solution of mixed tartrate of sodium and potassium is added.

The desired product is extracted by addition of ethyl ether. The organic phase is washed with water, dried with magnesium sulfate and concentrated using a rotary evaporator. The product is purified by chromatography on a silica column, eluted with a heptane/ethyl acetate 9:1 mixture. After evaporation of the solvents, 13.7 g (90%) of the expected compound are recovered in the form of a yellow oil.

(4-Iodo-2-propoxyphenyl)methanol

The procedure is the same as that described above, using 14 g of methyl 4-iodo-2-propoxybenzoate, 450 ml of toluene and 87.5 ml of DiBAlH. The product is purified by chromatography on a silica column, eluted with a heptane/ethyl acetate 9:1 mixture. After evaporation of the solvents, 11.3 g (88%) of the expected compound are recovered in the form of a yellow oil.

(4-Iodo-2-phenethyloxyphenyl)methanol

The procedure is the same as that described above, using 16.7 g of methyl 4-iodo-2-phenethyl oxybenzoate, 450 ml of toluene and 87.5 ml of DiBAlH. After evaporation of the solvents, 15.4 g (100%) of the expected compound are recovered in the form of a red oil.

(2-Benzyloxy-4-iodophenyl)methanol

The procedure is the same as that described above, using 14 g of methyl 2-benzyloxy-4-iodobenzoate, 350 ml of toluene and 72 ml of DiBAlH. The product is purified by chromatography on a silica column, eluted with a heptane/ethyl acetate 9:1 mixture. After evaporation of the solvents, 12.2 g (99%) of the expected compound are recovered in the form of a yellow oil.

Oxidation of the Alcohols:

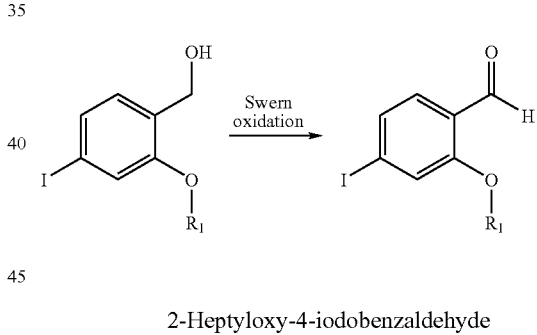

2-Heptyloxy-4-iodobenzaldehyde

A solution of dimethyl sulfoxide (3 ml, 41.4 mmol) in dichloromethane is added to a solution of oxalyl chloride (20.7 mmol, 1.8 ml) in dichloromethane (55 ml). A solution of (2-heptyloxy-4-iodophenyl)methanol (6.55 g, 18.8 mmol) in 25 ml of dichloromethane is added dropwise to the solution previously obtained, at −78° C. The mixture is stirred until the temperature returns to room temperature. The organic phase is acidified with a 2N hydrochloric acid solution. The desired product is extracted by addition of ethyl acetate. The organic phase is washed with water, dried with magnesium sulfate and concentrated using a rotary evaporator. 6.5 g (100%) of the expected compound are recovered in the form of a yellow solid.

$^1$H NMR/CDCl$_3$: 0.9 (t, 3H); 1.2 to 1.4 (m, 4H); 1.5 (m, 2H); 1.8 (m, 2H); 4 (t, 2H); 7.3 (d, 1H); 7.4 (dd, 1H); 7.5 (d, 1H); 11.4 (s, 1H).

4-Iodo-2-propoxybenzaldehyde

The procedure is the same as that described above, using 5.5 g, that is 18.8 mmol, of (4-iodo-2-propoxyphenyl)methanol, 1.8 ml of oxalyl chloride and 3 ml of DMSO. After evaporation of the solvents, 5.5 g (100%) of the expected compound are recovered in the form of a yellow solid.

$^1$H NMR/CDCl$_3$: 1.1 (t, 3H); 1.9 (m, 2H); 4 (t, 2H); 7.3 (d, 1H); 7.4 (dd, 1H); 7.5 (d, 1H); 11.4 (s, 1H).

4-Iodo-2-phenethyloxybenzaldehyde

The procedure is the same as that described above, using 6.6 g, that is 18.8 mmol, of (4-iodo-2-phenethyloxyphenyl)methanol, 1.8 ml of oxalyl chloride and 3 ml of DMSO. After evaporation of the solvents, 6.4 g (96%) of the expected compound are recovered in the form of a yellow solid.

$^1$H NMR/CDCl$_3$: 3.1 (t, 2H); 4.3 (t, 2H); 7.3 to 7.4 (m, 7H); 7.5 (d, 1H); 11.4 (s, 1H).

2-Benzyloxy-4-iodobenzaldehyde

The procedure is the same as that described above, using 12.15 g, that is 35.7 mmol, of (2-benzyl oxy-4-iodophenyl)methanol, 3.5 ml of oxalyl chloride in 100 ml of dichloromethane and 5.6 ml of DMSO in 20 ml of dichloromethane. After evaporation of the solvents, 11.6 g (96%) of the expected compound are recovered in the form of a yellow solid.

$^1$H NMR/CDCl$_3$: 5.18 (s, 2H); 7.4 to 7.5 (m, 7H); 7.6 (d, 1H); 11.5 (s, 1H).

Grafting of fmoc-(4-aminophenyl)acetic acid

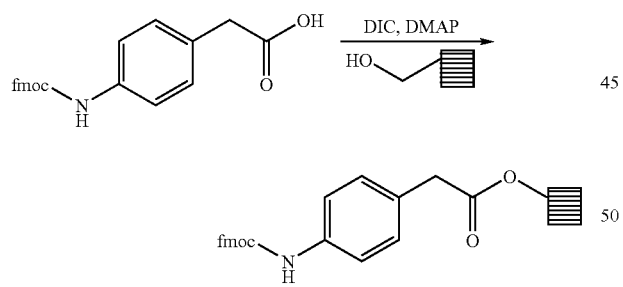

4 ml of a solution of DMF (28 ml), 4-dimethylaminopyridine (DMAP) (103 mg, 0.12 mmol), diisopropylcarbodiimide (DIC) (2.6 ml, 3.6 mmol) in dichloromethane (2.6 ml) are diluted with 16 ml of dichloromethane. 1.34 g (3.6 mmol) of fmoc-(4-aminophenyl)acetic acid and 80 Mimotope synphase-PS lanterns coupled to a hydroxymethylphenoxy (reference: SPPSLHMP, 15 µmol per lantern) introduced. The solution is slowly stirred for 12 hours at 50° C. The lanterns are filtered and washed twice with DMF, twice with a dichloromethane/methanol 5:5 solution and finally dichloromethane and dried.

Deprotection of the grafted fmoc-(4-aminophenyl)acetic acid

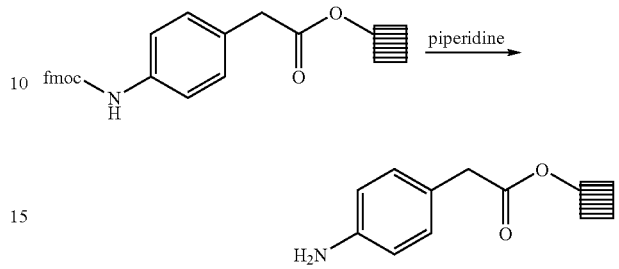

The lanterns previously obtained are stirred in a 20% solution of piperidine in DMF (about 30 ml) for 1.5 hours. The lanterns are filtered and washed twice with DMF, twice with a dichloromethane/methanol 5:5 solution and finally dichloromethane and dried.

Reductive Amination:

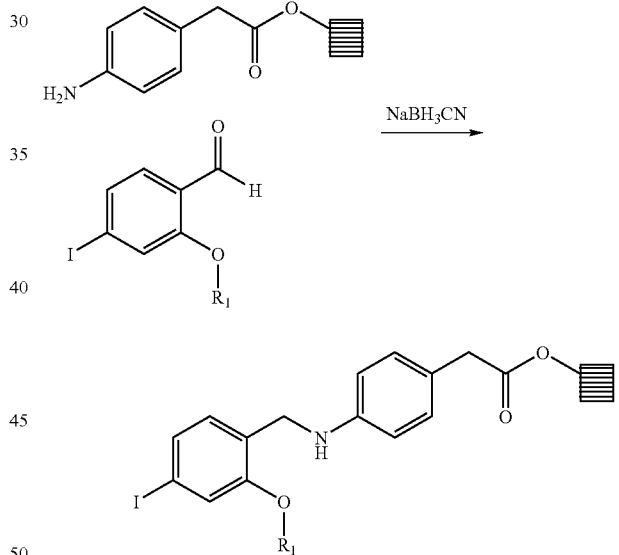

240 lanterns previously grafted with fmoc-(4-aminophenyl)acetic acid and whose fmoc-amino group has been deprotected are identified by a transponder and then distributed into flasks containing various solutions of aldehydes B5 to B8. The mixture is stirred at room temperature for 12 hours. A solution (noted 1 in the table) of sodium cyanoborohydride (236 mg, 3.75 mmol) in 37.5 ml of DMF and 375 µl of acetic acid is added to each flask. The resulting solution is stirred at 60° C. for 12 hours. The lanterns are filtered and the reduction with cyanoborohydride is started again under the same conditions. The lanterns are filtered and washed twice with DMF, twice with a solution of dichloromethane/methanol 5:5 and finally dichloromethane and dried.

|    | Aldehydes (300 µl/l) | MM | [C] | Number lanterns | mmol introduced | Mass (g) | vol DMF (ml) | vol AcOH (µl) |
|----|---------------------|--------|------|----|------|-------|-------|-----|
| B5 | 2-Heptyloxy-4-iodo-benzaldehyde | 346.21 | 0.50 | 60 | 9.00 | 3.116 | 18.00 | 180 |
| B6 | 2-Benzyloxy-4-iodo benzaldehyde | 338.14 | 0.50 | 60 | 9.00 | 3.043 | 18.00 | 180 |
| B7 | 4-Iodo-2-phenethyloxy-benzaldehyde | 352.17 | 0.50 | 60 | 9.00 | 3.170 | 18.00 | 180 |
| B8 | 4-Iodo-2-propoxy-benzaldehyde | 290.10 | 0.50 | 60 | 9.00 | 2.611 | 18.00 | 180 |
| 1  | NaBH$_3$CN (625 µl/l) | 62.84 | 0.1 | 60 | 3.75 | 0.236 | 37.5 | 375 |

Coupling with the Thiol:

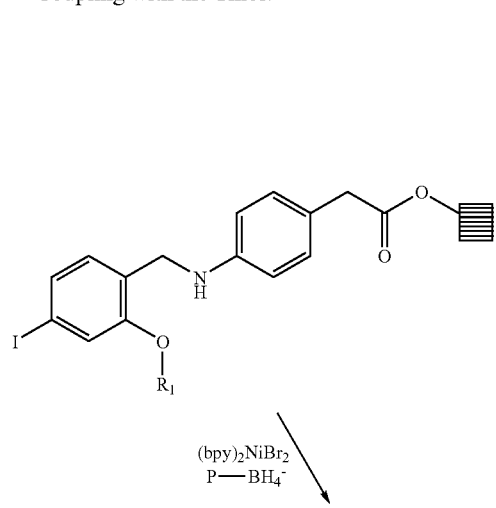

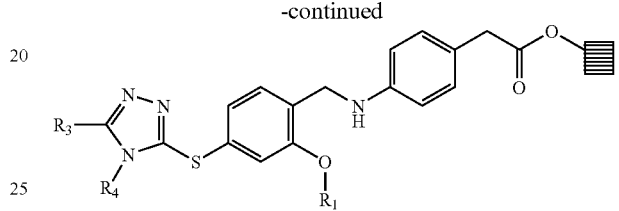

-continued

A mixture of borohydride, polymer-supported resin Amberlite® IRA400 (2.5 mmol/g) (Aldrich: 32864-2) (9.6 g), bis(bipyridine)nickel (II) bromide (*Organometallics*, 4, (1985), 657-661) (576 mg, 0.001 mmol), of the corresponding thiol (see quantities in Table I below) and of 48 lanterns previously grafted with the corresponding iodinated derivatives (obtained by reductive amination) in an ethanol/THF (24 ml/24 ml) mixture is stirred at 70° C. for 12 hours. The lanterns are filtered and washed twice with DMF, twice with a solution of dichloromethane/methanol 5:5 and finally dichloromethane and dried.

TABLE I

| Thiols | | Molar mass | Concentration | Number of lanterns | Mmol present | Mass (g) | EtOH/THF 1/1 vol (ml) |
|---|---|---|---|---|---|---|---|
| ![structure] | 5-(4-tert-Butyl-phenyl)-4-methyl-4H-[1,2,4]triazole-3-thiol | 247.36 | 0.50 | 48 | 24.000 | 5.94 | 48.000 |
| ![structure] | 4-Methyl-4H-[1,2,4]triazole-3-thiol | 115.16 | 0.50 | 48 | 24.000 | 2.76 | 48.000 |
| ![structure] | 5-(4,5-Dichloro-imidazol-1-ylmethyl)-4-methyl-4H-[1,2,4]triazole-3-thiol | 264.14 | 0.50 | 48 | 24.000 | 6.34 | 48.000 |

TABLE I-continued

| Structure | Name | | | | | | |
|---|---|---|---|---|---|---|---|
| 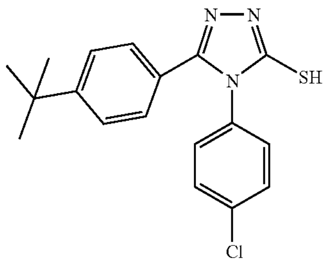 | 5-(4-tert-Butyl-phenyl)-4-(4-chloro-phenyl)-4H-[1,2,4]triazole-3-thiol | 343.88 | 0.50 | 48 | 24.000 | 8.25 | 48.000 |
| 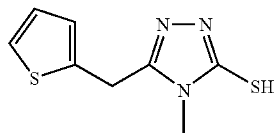 | 4-Methyl-5-thiophen-3-ylmethyl-4H-[1,2,4]triazole-3-thiol | 211.31 | 0.50 | 48 | 24.000 | 5.07 | 48.000 |
| 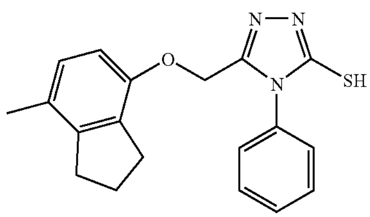 | 5-(7-Methyl-indan-4-yloxymethyl)-4-phenyl-4H-[1,2,4]triazole-3-thiol | 337.44 | 0.50 | 48 | 24.000 | 8.1 | 48.000 |
| ResinBH4- | | 2.5 mmol/g | 1 eq | 48 | 24.000 | 9.60 | |
| NiBr2(bpy)2 | | 530.87 | 12 mg/L | 48 | 0.00109 | 0.576 | |

Cleavage:

Each of the lanterns previously identified is individually cleaved with a solution of trifluoroacetic acid in dichloromethane (1.5 to 2 ml). After concentration, the products are individually analyzed by HPLC/Mass (see the following Table II).

TABLE II

| EXAMPLE | HPLC (% total of the surface area) | MASS ES (M + H+) |
|---|---|---|
| 2 | 89.00% | 601 |
| 3a | 85.00% | 607 |
| 4a | 89.00% | 593 |
| 5a | 90.00% | 545 |
| 6a | 86.00% | 469 |
| 7a | 83.00% | 474 |
| 8a | 63.00% | 461 |
| 9a | 78.00% | 413 |
| 10a | 90.00% | 617 |
| 11a | 89.00% | 623 |
| 12a | 88.00% | 609 |
| 13a | 81.00% | 689 |
| 14a | 86.00% | 703 |
| 15a | 83.00% | 641 |
| 16a | 100.00% | 565 |
| 17a | 95.00% | 5% (565) |
| 18a | 100.00% | 571 |
| 19a | 100.00% | 509 |
| 20a | 100.00% | 691 |
| 21a | 92.00% | 683 |
| 22a | 100.00% | 697 |
| 23a | 92.00% | 635 |

Example 25

Synthesis of 2-(4-{4-[5-(4-tert-Butylphenyl)-4-methyl-4H-[1,2,4]-triazol-3-ylsulfanyl]-2-heptyloxy-benzyl amino}phenyl)-N-hexylacetamide

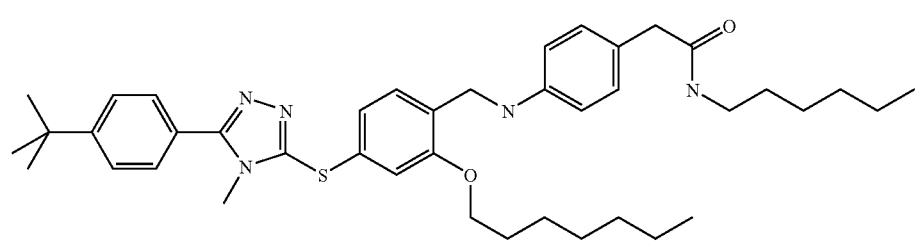

A solution of (4-{4-[5-(4-tert-butylphenyl)-4-methyl-4H-[1,2,4]-triazol-3-ylsulfanyl]-2-heptyloxybenzyl amino}phenyl)acetic acid (0.3 g, 0.5 mmol), benzotriazol-1-ol (0.074 g, 0.55 mmol) in dimethylformamide (10 ml) is stirred for 20 minutes. n-Hexylamine (0.066 ml, 0.5 mmol) and (3-dimethylaminopropyl)ethylcarbodiimide (0.105 g, 0.55 mmol) are added and then the medium is stirred for 24 hours at room temperature. The addition of water causes the formation of a precipitate which is dried before being purified by chromatography on a silica column, eluted with a heptane/ethyl acetate (3/7) mixture. After evaporation of the solvents, 0.205 g (60%) of the expected compound is recovered.

$^1$H NMR/DMSO$_{D6}$, 400 MHz: δ=0.84 (m, 3H); 1.26 to 1.39 (m, 8H); 1.33 (s, 9H); 1.4 (m, 2H); 1.7 (m, 2H); 2.98 (m, 2H); 3.16 (s, 2H); 3.65 (s, 3H); 4 (t, 2H); 4.17 (s, 2H); 6.45 (d, J=7.6 Hz, 2H); 6.80 (d, J=7.9 Hz, 1H); 6.1 (d, J=8.1 Hz, 2H); 6.96 (s, 1H); 7.21 (d, J=7.8 Hz, 2H); 7.58 (d, J=8.3 Hz, 2H); 7.69 (d, J=8.3 Hz, 2H); 7.79 (p, 1H).

HPLC/MS: 90% [684]

Example 26

Synthesis of 2-(4-{4-[5-(4-tert-Butylphenyl)-4-methyl-4H-[1,2,4]-triazol-3-ylsulfanyl]-2-heptyloxybenzyl amino}phenyl)-1-morpholin-4-ylethanone

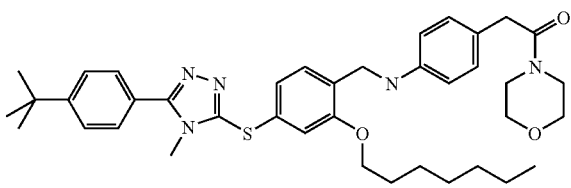

Same procedure as for Example 25. After evaporation of the solvents, 0.261 g (78%) of the expected compound is recovered.

$^1$H NMR/DMSO$_{D6}$, 400 MHz: δ=0.84 (m, 6H); 1.21 to 1.33 (m, 6H); 1.33 (s, 9H); 1.42 (m, 2H); 1.72 (m, 2H); 2.31 (s, 1H); 2.56 (s, 1H); 3.42 (s, 4H); 3.50 (s, 4H); 3.65 (s, 3H); 4.00 (s, 2H); 4.17 (s, 2H); 5.8-6.1 (p, 1H); 6.47 (d, J=7.7 Hz, 2H); 6.81 (d, J=7.5 Hz, 1H); 6.89 (d, J=7.6 Hz, 2H); 6.96 (s, 1H); 7.17-7.26 (m, 2H); 7.58 (d, J=8.0 Hz, 2H); 7.69 (d, J=7.9 Hz, 2H).

HPLC/MS: 97% [669]

Example 27

Synthesis of 2-(4-{4-[5-(4-tert-Butylphenyl)-4-methyl-4H-[1,2,4]-triazol-3-ylsulfanyl]-2-heptyloxybenzyl amino}phenylacetamide

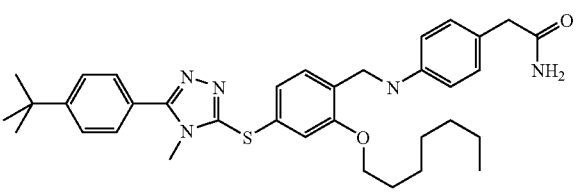

152 mg (1.12 mmol, 1.5 eq) of benzotriazol-1-ol, 497 mg (1.12 mmol, 1.5 eq) of benzotriazol-1-yloxytris(dimethylamino)phosphonium hexafluorophosphate, 780 µl (4.50 mmol, 4 eq) of diisopropylethylamine and finally 80 mg (1.50 mmol, 2 eq) of ammonium chloride are added to a solution of 450 mg (0.75 mmol, 1 eq) of (4-{4-[5-(4-tert-butylphenyl)-4-methyl-4H-[1,2,4]-triazol-3-ylsulfanyl]-2-heptyloxybenzyl amino}phenyl)acetic acid in 6 ml of dimethylformamide. The reaction mixture is stirred at room temperature for 24 hours, and then supplemented with a small amount of water. The precipitate obtained is filtered, dried and chromatographed on a silica gel cartridge (heptane/ethyl acetate 30/70). 298 mg (66%) of the expected compound are obtained.

$^1$H NMR/DMSO$_{D6}$, 400 MHz: δ=0.85 (t, J=6.8 Hz, 3H); 1.24-1.34 (m, 6H); 1.33 (s, 9H); 1.43 (m, 2H); 1.73 (m, 2H); 3.14 (s, 2H); 3.65 (s, 3H); 4.00 (t, j=6.3 Hz, 2H); 4.17 (d, j=5.9 Hz, 2H); 5.94 (t, 1H); 6.44 (d, j=8.5 Hz, 2H); 6.72 (s large, 1H); 6.81 (dd, j1=1.6 Hz, j2=7.9 Hz, 1H), 6.92 (d, j=8.4 Hz, 2H); 6.95 (d, j=1.6 Hz, 1H); 7.21 (d, j=7.9 Hz, 1H); 7.25 (s large, 1H); 7.58 (dd, j1=1.8 Hz, j2=6.7 Hz, 2H); 7.69 (dd, j1=1.9 Hz, j2=6.6 Hz, 2H);

$^{13}$C NMR/DMSO$_{D6}$, 400 MHz: δ=14.82 (CH$_3$); 22.90 (CH$_2$); 26.38 (CH$_2$); 29.27 (CH$_2$); 29.38 (CH$_2$); 31.81 (3CH$_3$); 32.11 (CH$_2$); 33.08 (CH$_3$); 35.48 (C); 41.84 (CH$_2$); 42.36 (CH$_2$); 68.68 (CH$_2$); 112.77 (2CH); 121.65 (CH); 124.47 (C); 125.15 (C); 126.54 (2CH); 128.70 (C); 129.10 (CH); 129.61 (CH); 130.37 (CH); 131.62 (CH); 147.89 (C); 148.71 (C); 153.69 (C); 156.87 (C); 157.56 (C); 173.85 (C).

HPLC/MS: 95% [600.3]

Example 28

Synthesis of 2-(4-{4-[5-(4-tert-Butylphenyl)-4-methyl-4H-[1,2,4]-triazol-3-ylsulfanyl]-2-heptyloxybenzyl amino}phenyl)-N-ethylacetamide

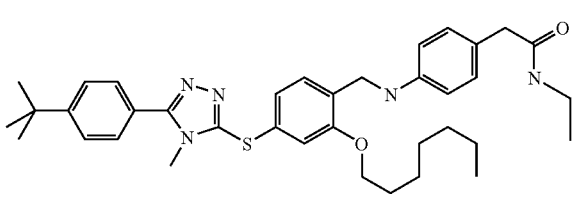

Same procedure as for Example 27. After evaporation of the solvents, 0.366 g (78%) of the expected compound is recovered.

$^1$H NMR/DMSO$_{D6}$, 400 MHz: δ=0.85 (t, J=7.0 Hz, 3H); 0.98 (t, J=7.2 Hz, 3H); 1.24-1.33 (m, 6H); 1.33 (s, 9H); 1.43 (m, 2H); 1.72 (m, 2H); 3.00-3.04 (qd, 2H); 3.15 (s, 2H); 3.65 (s, 3H); 4.00 (t, j=6.3 Hz, 2H); 4.16 (d, j=5.8 Hz, 2H); 5.95 (t, 1H); 6.81 (dd, j1=1.6 Hz, j2=7.9 Hz, 1H), 6.90 (d, j=8.4 Hz, 2H); 6.95 (d, j=1.6 Hz, 1H); 7.21 (d, j=7.9 Hz, 1H); 7.58 (dd, j1=1.9 Hz, j2=6.7 Hz, 2H); 7.69 (dd, j1=1.9 Hz, j2=6.6 Hz, 2H); 7.82 (t, 1H)

$^{13}$C NMR/DMSO$_{D6}$, 400 MHz: δ=14.29 (2CH$_3$); 15.10 (CH$_3$); 22.37 (CH$_2$); 25.87 (CH$_2$); 28.74 (CH$_2$); 28.86 (CH$_2$); 31.29 (3CH$_3$); 31.59 (CH$_2$); 32.56 (CH$_3$); 33.72 (CH$_2$); 34.96 (C); 40.36 (CH$_2$); 42.02 (CH$_2$); 68.17 (CH$_2$); 112.27 (2CH); 121.13 (CH); 123.96 (C); 124.63 (C); 126.02 (3CH); 128.19

(C); 128.58 (2CH); 129.12 (CH); 129.74 (2CH); 131.12 (C); 147.38 (C); 148.18 (C); 153.18 (C); 156.35 (C); 157.05 (C); 170.81 (C).

HPLC/MS: 94% [628.3]

Example 29

Synthesis of {4-[4-(5-Heptyl-4-methyl-4H-[1,2,4]-triazol-3-ylsulfanyl]-2-heptyloxybenzyloxy]phenyl}acetic acid methyl ester a. Preparation of 5-Heptyl-4-methyl-4H-[1,2,4]-triazole-3-thiol

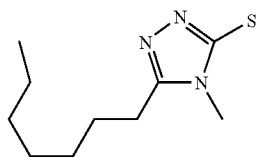

5 g (30.74 mmol, 1 eq) of octanoyl chloride and 3.58 g (33.81 mmol, 1.1 eq) of 4-methyl-3-thiosemicarbazide in solution in 350 ml of tetrahydrofuran are stirred for 3 hours at room temperature. The solution is concentrated to dryness. The solid obtained is taken up in 350 ml of a 10% aqueous potassium hydroxide solution 35 g (0.82 mmol, 20 eq). The reaction mixture is stirred overnight under reflux. In the cold state, the reaction medium is acidified. The precipitate obtained is filtered, washed with a minimum of water and then dried. 5.94 g (90%) of the expected compound are obtained.

$^1$H NMR (DMSO$_{D6}$, 400 MHz): δ=0.87 (t, J=7.0 Hz, 3H); 126-136 (m, 8H); 1.59-1.65 (2m, 2H); [2.19 (t)+2.64 (t, j=7.5 Hz), 2H]; [3.33 (s)+3.40 (s), 3H]; [11.95 (s) ~12%+13.45 (s) ~88%, 3H].

b. Synthesis of {4-[4-(5-Heptyl-4-methyl-4H-[1,2,4]-triazol-3-ylsulfanyl]-2-heptyloxybenzyloxy]phenyl}acetic acid methyl ester

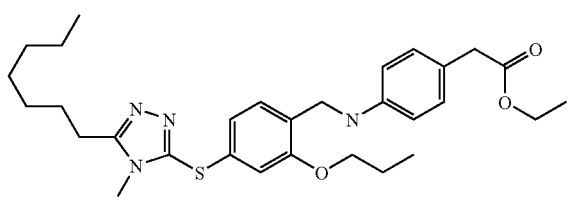

979 mg (2.45 mmol, 3 eq) of resin-supported borohydride and 11 mg (0.02 mmol, 0.03 eq) of bis(bipyridine)dibromonickel (II) are added to a solution of 244 mg (1.22 mmol, 1.5 eq) of 5-heptyl-4-methyl-4H-[1,2,4]-triazole-3-thiol in 4 ml of tetrahydrofuran/ethanol 5/5. To the suspension obtained there is added a solution of 405 mg (0.82 mmol, 1 eq) of [4-(2-heptyloxy-4-iodobenzyloxy)phenyl]acetic acid methyl ester in 4 ml of tetrahydrofuran/ethanol 5/5. The reaction mixture is stirred overnight under reflux. After returning to room temperature, the reaction medium is filtered and then concentrated. The residue is chromatographed on silica gel (heptane/ethyl acetate: gradient from 70/30 to 50/50). After concentration, 427 mg (92%) of the expected compound are obtained.

$^1$H NMR/DMSO$_{D6}$, 400 MHz: δ=0.82-0.87 (m, 6H); 1.18-1.33 (m, 17H); 1.64-1.68 (m, 4H); 2.75 (t, j=7.5 Hz, 2H); 3.49 (s, 2H), 3.59 (s, 2H); 3.60 (s, 3H); 3.95 (t, j=6.3 Hz, 2H); 3.98 (s, 2H); 6.70 (dd, j1=1.7 Hz, j2=7.9 Hz, 1H); 6.86 (d, j=1.6 Hz, 1H); 6.90 (dd, j1=2.0 Hz, j2=8.6 Hz, 2H); 7.16 (d, j=8.6 Hz, 2H); 7.34 (d, j=7.9 Hz, 1H)

$^{13}$C NMR/DMSO$_{D6}$, 400 MHz: δ=14.26 (CH$_3$); 14.27 (CH$_3$); 22.33 (CH$_2$); 22.41 (CH$_2$); 24.97 (CH$_2$); 25.73 (CH$_2$); 26.44 (CH$_2$); 28.70 (CH$_2$); 28.82 (CH$_2$); 28.84 (CH$_2$); 30.69 (CH$_3$); 31.53 (CH$_2$); 39.26 (C); 39.47 (CH$_2$); 51.94 (CH$_3$); 64.54 (CH$_2$); 68.30 (CH$_2$); 111.68 (CH); 114.81 (2CH); 120.10 (CH); 124.64 (C); 126.82 (C); 130.56 (CH); 130.69 (2CH); 133.92 (C); 146.04 (C); 157.23 (C); 157.64 (C); 157.69 (C); 172.16 (C).

HPLC/MS: 89% [582]

Example 30

Synthesis of {4-[2-Heptyloxy-4-(5-hexyl-4-methyl-4H-[1,2,4]-triazol-3-ylsulfanyl)benzyloxy]phenyl}acetic acid

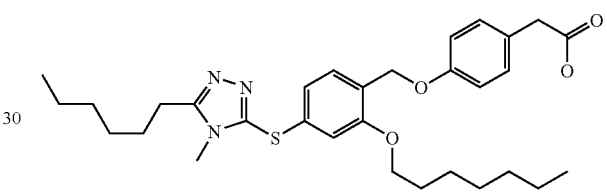

Same procedure as for Example 2. After evaporation of the solvents, 0.177 g (38%) of the expected compound is recovered.

$^1$H NMR (DMSO$_{D6}$, 400 MHz): δ=0.90 (t, J=7.1 Hz, 3H); 0.93 (t, J=6.8 Hz, 3H); 1.28-1.39 (m, 16H); 1.72-1.75 (m, 4H); 2.81 (t, j=7.7 Hz); 3.54 (s, 2H): 3.55 (s, 3H); 4.01 (t, j=6.3 Hz, 2H); 5.04 (s, 2H); 6.76 (d×d, j=7.9 Hz–j=1.7 Hz, 1H); 6.91 (d, J=1.6 Hz, 1H); 6.94-6.97 (m, 2H); 7.21 (d, j=8.7 Hz, 2H); 7.40 (d, J=7.9 Hz, 1H).

HPLC/MS 98% [568]

Example 31

Synthesis of {4-[4-(5-Heptyl-4-methyl-4H-[1,2,4]-triazol-3-ylsulfanyl)-2-propoxybenzylamino]phenyl}acetic acid ethyl ester a. Preparation of [4-(4-Iodo-2-propoxybenzylamino)phenyl]acetic acid ethyl ester

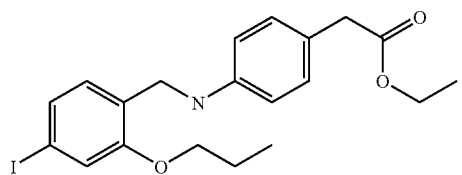

1.50 g (5.17 mmol, 1 eq) of 4-iodo-2-propoxybenzaldehyde in solution in 40 ml of dimethylformamide supplemented with 1% of acetic acid is added to a solution in 40 ml of dimethylformamide supplemented with 1% of acetic acid. The reaction mixture is stirred overnight at room temperature. 50 g (5.17 mmol, 1 eq) of sodium cyanoborohydride are added. The reaction medium is heated at 60° C. for 4 hours. After returning to room temperature, the reaction medium is supplemented with water and then extracted with ether. The organic phase is dried over magnesium sulfate, filtered and then concentrated. The residue is chromatographed on silica gel (heptane/ethyl acetate 80/20). 2.00 g (85%) of the expected compound are obtained.

$^1$H NMR (DMSO$_{D6}$, 400 MHz): δ=1.01 (t, J=7.4 Hz, 3H); 1.16 (t, J=7.1 Hz, 3H); 1.76 (m, 2H); 3.42 (s, 2H); 3.98-4.17 (m, 2×2H); 4.16 (d, J=6 Hz, 2H); 6.04 (t, j=6 Hz, 1H); 6.45 (d, J=8.5 Hz, 1H); 6.92 (d, j=8.5 Hz, 2H); 7.23 (dd, j1=7.9 Hz, j2=1.5 Hz, 1H); 7.27 (d, J=1.5 Hz, 1H).

b. Synthesis of {4-[4-(5-Heptyl-4-methyl-4H-[1,2,4]-triazol-3-ylsulfanyl)-2-propoxybenzylamino]phenyl}acetic acid ethyl ester

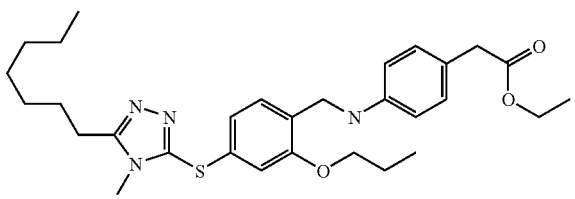

2.647 g (6.62 mmol, 3 eq) of resin-supported borohydride and 30 mg (0.06 mmol, 0.03 eq) of bis(bipyridine)dibromonickel (II) are added to a solution of 0.706 g (3.31 mmol, 1.5 eq) of 5-heptyl-4-methyl-4H-[1,2,4]-triazole-3-thiol in 10 ml of tetrahydrofuran/ethanol 5/5. To the suspension obtained there is added a solution of 100 mg (0.22 mmol, 1 eq) of ethyl [4-(4-iodo-2-propoxybenzylamino)phenyl]acetate in 10 ml of tetrahydrofuran/ethanol 5/5. The reaction mixture is stirred overnight under reflux. After returning to room temperature, the reaction medium is filtered, concentrated and then chromatographed on silica gel (heptane/ethyl acetate 40/60). After evaporation of the solvents, 0.750 g (63%) of the expected compound is recovered.

$^1$H NMR/DMSO$_{D6}$, 400 MHz: δ=0.91-0.94 (m, 3H); 1.06 (t, j=7.4 Hz, 3H); 1.22 (t, j=7.1 Hz, 3H); 1.31-1.38 (m, 8H); 1.67-1.87 (m, 4H); 2.79 (t, j=7.6 Hz, 2H); 3.47 (s, 2H); 3.53 (s, 3H); 3.98 (t, j=6.3 Hz, 2H); 4.09 (q, j=7.1 Hz, 2H); 4.22 (d, j=6.0 Hz, 1H); 6.08 (t, j=6.0 Hz, 1H); 6.51 (d, j=8.5 Hz, 2H); 6.74 (d, j=7.9 Hz, 1H); 6.89 (d, j=1.6 Hz, 1H); 6.97 (d, j=8.4 Hz, 2H); 7.23 (d, j=7.9 Hz, 1H)

$^{13}$C NMR/DMSO$_{D6}$, 400 MHz: δ=10.81 (CH$_3$); 14.28 (CH$_3$); 14.44 (CH$_3$); 22.32 (CH$_2$); 22.40 (CH$_2$); 24.96 (CH$_2$); 26.42 (CH$_2$); 28.68 (CH$_2$); 28.83 (CH$_2$); 30.66 (CH$_3$); 31.52 (CH$_2$); 39.86 (CH$_2$); 41.22 (CH$_2$); 60.33 (CH$_2$); 69.58 (CH$_2$); 111.74 (CH); 112.32 (2CH); 120.55 (CH); 121.64 (C); 127.80 (C); 129.06 (CH); 130.06 (2CH); 131.68 (C); 146.37 (C); 147.76 (C); 157.04 (C); 157.49 (C); 172.06 (C).

Example 32

Synthesis of {4-[2-Propoxy-4-(5-pyridin-4-yl-4H-[1,2,4]-triazol-3-ylsulfanyl)benzylamino]phenyl}acetic acid ethyl ester

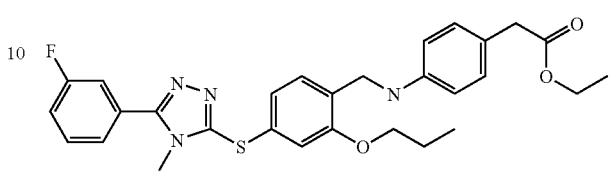

265 mg (0.66 mmol, 3 eq) of resin-supported borohydride and 3 mg (0.01 mmol, 0.03 eq) of bis(bipyridine)dibromonickel (II) are added to a solution of 69 mg (0.33 mmol, 1.5 eq) of 5-(3-fluorophenyl)-1H-[1,2,4]-triazole-3-thio in 1.5 ml of tetrahydrofuran/ethanol 5.5. To the suspension obtained there is added a solution of 100 mg (0.22 mol, 1 eq) of ethyl [4-(4-iodo-2-propoxybenzylamino)phenyl]acetate in 1.5 ml of tetrahydrofuran/ethanol 5/5. The reduction mixture is stirred overnight under reflux. After returning to room temperature, the reaction medium is filtered and then concentrated. 0.115 g (97%) of the expected compound is recovered.

$^1$H NMR (DMSO$_{D6}$, 400 MHz): δ=1.06 (t, J=7.3 Hz, 3H); 1.21 (t, J=7.1 Hz, 3H); 1.79-1.84 (m, 2H); 3.73 (s, 3H); 4.02-4.11 (m, 4H); 4.24 (d, J=6.1 Hz, 2H); 6.08 (t, J=6.1 Hz, 1H); 6.51 (d, J=8.5 Hz, 2H); 6.87 (dd, J1=1.7 Hz, J2=7.9 Hz, 1H); 6.97 (d, J=8.5 Hz, 2H); 7.07 (d, J=1.7 Hz, 1H); 7.26 (d, J=7.9 Hz, 1H); 7.48-7.50 (m, 1H); 7.66-7.70 (m, 3H).

$^{13}$C NMR/DMSO$_{D6}$, 400 MHz: δ=10.83 (CH$_3$); 12.04 (CH$_3$); 19.93 (CH$_2$); 30.21 (CH$_3$); 36.85 (CH$_2$); 38.86 (CH$_2$); 57.92 (CH$_2$); 67.27 (CH$_2$); 109.93 (CH); 110.18 (CH); 113.20 (CH); 113.44 (CH); 118.98 (CH); 119.26 (C); 122.72 (CH); 125.84 (C); 126.73 (CH); 127.04-127.18 (C); 127.67 (CH); 128.41 (C); 129.01 (CH); 129.10 (CH); 145.36 (C); 146.43 (C); 152.86 (C); 154.66 (C); 158.74 (C); 169.66 (C).

Example 33

Synthesis of {4-[4-(4-Methyl-5-pyridin-4-yl-4H-[1,2,4]-triazol-3-ylsulfanyl)-2-propoxybenzylamino]phenyl}acetic acid ethyl ester

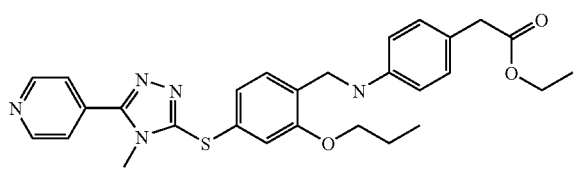

265 mg (0.66 mmol, 3 eq) of resin-supported borohydride and 3 mg (0.01 mmol, 0.03 eq) of bis(bipyridine)dibromonickel (II) are added to a solution of 64 mg (0.33 mmol, 1.5 eq) of 4-methyl-5-pyridin-4-yl-4H-[1,2,4]-triazole-3-thiol in 1.5 ml of tetrahydrofuran/ethanol 5/5. To the suspension obtained there is added a solution of 100 mg (0.22 mmol, 1 eq) of ethyl [4-(4-iodo-2-propoxybenzylamino)phenyl]acetate in 1.5 ml of tetrahydrofuran/ethanol 5/5. The reaction mixture is stirred overnight under reflux. After returning to room temperature, the reaction medium is filtered and then concentrated. 0.111 g (97%) of the expected compound is recovered.

$^1$H NMR (DMSO$_{D6}$, 400 MHz): δ=1.06 (t, J=7.3 Hz, 3H); 1.21 (t, J=7.1 Hz, 3H); 1.81 (q, J=6.5 Hz, 2H); 3.46 (s, 2H); 3.79 (s, 3H), 4.02-4.20 (m, 4H); 4.24 (d, J=6 Hz, 2H); 6.08 (t, J=6 Hz, 1H), 6.51 (D, J=8.5 Hz, 2H); 6.89 (Dd, J1=1.69 Hz, J2=7.9 Hz, 1H); 6.97 (d, j=8.5 Hz, 1H); 7.09 (d, J=1.69 Hz, 1H); 7.26 (D, j=7.9 Hz, 1H); 7.85 (Dd, J1=1.33, J2=4.25 Hz, 2H), 8.83 (Dd, J1=1.33, J2=4.25 Hz, 2H).

HPLC/MS 97% [519]

Example 34

Synthesis of {4-[4-(5-Heptyl-4-methyl-4H-[1,2,4]-triazol-3-ylsulfanyl)-2-propoxybenzylamino]phenyl}acetic acid

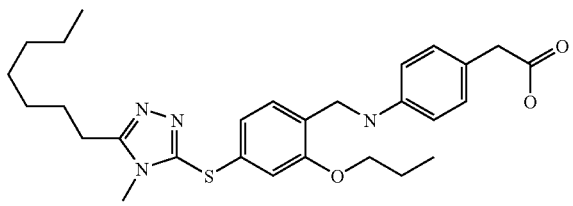

A solution of {4-[4-(5-heptyl-4-methyl-4H-[1,2,4]-triazol-3-ylsulfanyl)-2-propoxybenzylamino]phenyl}acetic acid ethyl ester obtained in Example 31 (0.7 g, 2.39 mmol), 2M aqueous potassium carbonate (9 ml) in methanol (20 ml) is heated under reflux for 3 hours. The reaction medium is acidified at room temperature with a 2N hydrochloric acid solution to pH 5. The desired product is extracted by addition of ethyl acetate. The organic phase is washed with water, dried over magnesium sulfate. After evaporation of the solvents, 0.592 g (89%) of the expected compound are recovered in the form of a yellow amorphous solid.

$^1$H NMR (DMSO$_{D6}$, 400 MHz): δ=0.93 (t, j=4.4 Hz, 3H); 1.24 (t, j=7.2 Hz, 3H); 1.31-1.37 (m, 8H); 1.70-1.81 (m, 4H); 2.78 (t, j=7.6 Hz, 2H); 3.40 (s, 2H); 3.53 (s, 3H); 3.98 (t, j=6.4 Hz, 2H); 4.22 (s, 2H); 6.04 (s large, 1H); 6.50 (d, j=8.5 Hz, 2H); 6.73 (dd, j1=8.0 Hz, j2=1.6 Hz, 1H); 6.89 (d, j=1.6 Hz, 1H); 6.96 (d, j=8.4 Hz, 2H); 7.23 (d, j=7.9 Hz, 1H); 12.17 (s large, 1H).

Example 35

Synthesis of {4-[2-Propoxy-4-(5-pyridin-4-yl-4H-[1,2,4]-triazol-3-ylsulfanyl)benzylamino]phenyl}acetic acid

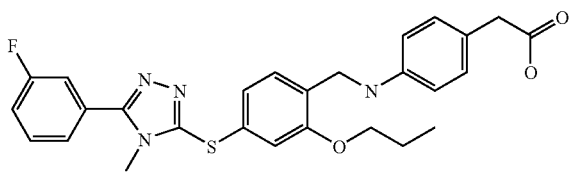

Same procedure as that followed in Example 34, using the ester obtained in Example 32. After evaporation of the solvents, 0.043 g (47%) of the expected compound is recovered.

$^1$H NMR (CDCl$_3$, 400 MHz): δ=0.94 (t, j=7.4 Hz, 3H); 1.69-1.76 (m, 2H); 3.42 (s, 2H); 3.57 (s, 3H); 3.82 (t, j=6.0 Hz, 2H); 4.22 (s, 2H); 6.54 (d, j=7.7 Hz, 2H); 6.81 (d, j=7.2 Hz, 1H); 6.88 (s, 1H); 6.98 (d, j=7.8 Hz, 2H); 7.11-7.19 (m, 2H); 7.29-7.43 (m, 3H)

Example 36

Synthesis of {4-[4-(4-Methyl-5-pyridin-4-yl-4H-[1,2,4]-triazol-3-ylsulfanyl)-2-propoxybenzylamino]phenyl}acetic acid

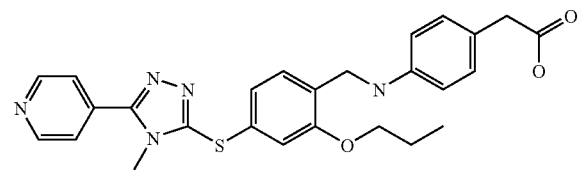

Same procedure as that followed in Example 34, using the ester obtained in Example 33. After evaporation of the solvents, 0.070 g (74%) of the expected compound is recovered.

$^1$H NMR (CDCl$_3$, 400 MHz): δ=1.25 (t, J=7.2 Hz, 3H); 1.80 (q, J=6.5 Hz, 2H); 3.52 (s, 2H); 3.69 (s, 3H); 3.93 (t, J=6.4 Hz, 2H); 4.30 (s, 2H); 6.56 (D, J=6.4 Hz, 2H); 6.91 (Dd, J1=1.68 Hz, J2=7.8 Hz, 1H); 6.99 (d, j=7.8 Hz, 1H); 7.05 (D, j=8.5 Hz, 2H); 7.24 (D, J=7.8 Hz, 1H); 7.63 (Dd, J1=1.64, J2=4.48 Hz, 2H), 8.78 (Dd, J=1.64, J2=4.48 Hz, 2H).

Example 37

Cross Curve PPAR Transactivation Test

The activation of receptors with an agonist (activator) in HeLN cells leads to the expression of a reporter gene, luciferase, which, in the presence of a substrate, generates light. The modulation of the receptors is measured as quantity of luminescence produced after incubating the cells in the presence of a reference agonist. The ligands will displace the agonist from its site. The measurement of the activity is performed by quantification of the light produced. This measurement makes it possible to determine the modulatory activity of the compounds according to the invention by determining the constant which is the affinity of the molecule for the receptor. Since this value can fluctuate according to the basal activity and the expression of the receptor, it is called apparent Kd (Kd app in nM).

To determine this constant, the cells are in contact with a concentration of the product to be tested and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyridin-2-ylamino)ethoxy]benzyl}thiazolidine-2,4-dione for PPARγ. Measurements are also carried out for the controls total agonist with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates in an amount of 10 000 cells per well in 100 μl of DMEM medium free of phenol red and supplemented with 10% lipid-free calf serum. The plates are then incubated at 37° C., 7% CO$_2$ for 16 hours.

The various dilutions of the test products and of the reference ligand are added in an amount of 5 μl per well. The plates are then incubated for 18 hours at 37° C., 7% $CO_2$. The culture medium is removed by turning over and 100 µl of a 1:1 PBS/Luciferin mixture are added to each well. After 5 minutes, the plates are read by the luminescence reader.

These cross curves make it possible to determine the $AC_{50}$ values (concentrations at which 50% activation is observed) for the reference ligand at various concentrations of test product. These $AC_{50}$ values are used to calculate the Schild regression by plotting a straight line corresponding to the Schild equation ("*Quantitation in Receptor Pharmacology*" Terry P. Kenakin, *Receptors and Channels*, 2001, 7, 371-385) which leads to Kd app values being obtained (in nM).

Transactivation Results:

| Compound | PPAR α Kd app (nM) | PPARs δ Kd app (nM) | PPAR γ Kd app (nM) |
|---|---|---|---|
| Example 1 | n.a. | n.a. | 60 |
| Example 2 | 8000 | n.a. | 15 | n.a. means not active

The results obtained with the compounds according to the invention indeed show Kd app values ≦100 nM for at least one of the receptor subtypes. The compounds according to the invention are therefore indeed modulators of the PPAR receptors.

Example 38

Compositions

Various specific formulations based on the compounds according to the invention are illustrated in this example.

A—Oral Route:
(a) 0.2 g Tablet:

| | |
|---|---|
| Compound of Example 1 | 0.001 g |
| Starch | 0.114 g |
| Bicalcium phosphate | 0.020 g |
| Silica | 0.020 g |
| Lactose | 0.030 g |
| Talc | 0.010 g |
| Magnesium stearate | 0.005 g |

(b) Oral Suspension in 5 ml Vials:

| | |
|---|---|
| Compound of Example 2 | 0.001 g |
| Glycerine | 0.500 g |
| Sorbitol at 70% | 0.500 g |
| Sodium saccharinate | 0.010 g |
| Methyl para-hydroxybenzoate | 0.040 g |
| Flavoring | qs |
| Purified water | qs 5 ml |

(c) 0.8 g Tablet:

| | |
|---|---|
| Compound of Example 5 | 0.500 g |
| Pregelatinized starch | 0.100 g |
| Microcrystalline cellulose | 0.115 g |
| Lactose | 0.075 g |
| Magnesium stearate | 0.010 g |

(d) Oral Suspension in 10 ml Vials:

| | |
|---|---|
| Compound of Example 7 | 0.200 g |
| Glycerine | 1.000 g |
| Sorbitol at 70% | 1.000 g |
| Sodium saccharinate | 0.010 g |
| Methyl para-hydroxybenzoate | 0.080 g |
| Flavoring | qs |
| Purified water | qs 10 ml |

B—Topical Route:
(a) Salve:

| | |
|---|---|
| Compound of Example 4 | 0.020 g |
| Isopropyl myristate | 81.700 g |
| Fluid liquid paraffin | 9.100 g |
| Silica ("Aerosil 200" marketed by DEGUSSA) | 9.180 g |

(b) Salve:

| | |
|---|---|
| Compound of Example 6 | 0.300 g |
| Petroleum jelly | qs 100 g |

(c) Nonionic Water-In-Oil Cream:

| | |
|---|---|
| Compound of Example 8 | 0.100 g |
| Mixture of emulsifying lanolin alcohols, waxes and oils ("anhydrous eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 20 | 0.100 g |
| Polyethylene glycol (PEG 400) | 69.900 g |
| Ethanol at 95% | 30.000 g |

(e) Hydrophobic Salve:

| | |
|---|---|
| Compound of Example 12 | 0.300 g |
| Isopropyl myristate | 36.400 g |
| Silicone oil ("Rhodorsil 47 V 300" marketed by RHONE-POULENC) | 36.400 g |
| Beeswax | 13.600 g |
| Silicone oil ("Abil 300,000 cst" marketed by GOLDSCHMIDT) | qs 100 g |

(f) Nonionic Oil-In-Water Cream:

| | |
|---|---|
| Compound of Example 1 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |

| | |
|---|---|
| -continued | |
| Propyl para-hydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is suited that the scope of the present invention be limited solely by the scope of the following claims, including equivalents thereof.

What is claimed is:

1. A compound having the following structural formula (I):

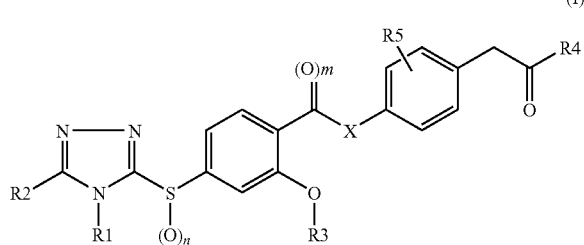

in which:
- $R_1$ is a hydrogen atom, an alkyl radical, an aryl or heteroaryl radical, or an aralkyl radical;
- $R_2$ is a hydrogen atom, an alkyl radical optionally substituted with an aryl radical or with a heteroaryl radical, a radical —$CH_2OR_6$, or an aryl radical; $R_6$ is as defined below;
- X is —S—, —Se—, —O— or —N—$R_7$;
- $R_7$ is as defined below;
- $R_3$ is an alkyl radical or an aralkyl radical;
- $R_4$ is a hydroxyl radical, an alkoxyl radical or the radical —N($R_8,R_9$);
- $R_8$ and $R_9$ are as defined below;
- $R_5$ is a hydrogen atom, a halogen atom, an alkyl radical, an alkoxyl radical or a hydroxyl radical;
- $R_6$ is an aryl radical or a heteroaryl radical;
- $R_7$ is a hydrogen atom, an alkyl radical, an aralkyl radical, or a radical —C(Y)$R_{10}$;
- $R_{10}$ is as defined below;
- $R_8$ and $R_9$, which may be identical or different, are each a hydrogen atom, an alkyl radical, or together form, with the nitrogen atom from which they depend, a morpholino, piperidino or pyrrolidino group;
- $R_{10}$ is a hydrogen atom, an alkyl radical, an alkoxyl radical, or a radical —$NR_{11}$;
- $R_{11}$ is as defined below;
- $R_{11}$ is a hydrogen atom, an alkyl radical or an aralkyl radical;
- Y is an oxygen or a sulfur atom;
- n is an integer ranging from 0 to 2;
- m is 0 or 1;

and when X is S or Se and m is 0, then n is 0,
and the isomers, tautomers, N-oxides and salts thereof.

2. The compound as defined by claim 1, wherein formula (I), X is —S—.

3. The compound as defined by claim 1, wherein formula (I), X is —Se—.

4. The compound as defined by claim 1, wherein formula (I), X is —O—.

5. The compound as defined by claim 1, wherein formula (I), X is —N—$R_7$.

6. An alkali metal or alkaline-earth metal, zinc or organic amine salt of the compound as defined by claim 1.

7. The compound as defined by claim 1, wherein the alkyl radical is selected from the group consisting of optionally substituted methyl, ethyl, n-propyl, isopropyl, n-butyl, isobutyl, tert-butyl, n-pentyl, hexyl, octyl, decyl, dodecyl and cyclohexyl radicals.

8. The compound as defined by claim 1, wherein the alkoxyl radical is selected from the group consisting of methoxyl, ethoxyl, isopropyloxyl, tert-butoxyl, hexyloxyl, benzyloxyl and phenoxyl radicals, each being optionally substituted with one or more alkyl radicals.

9. The compound as defined by claim 1, wherein the aryl radical is selected from the group consisting of phenyl, biphenyl and naphthyl radicals, optionally fused with one or more other rings and optionally mono- or disubstituted with one or more atoms, groups, functional groups or radicals selected from among a halogen atom, a $CF_3$ radical, an alkyl radical, an alkoxyl radical, or a nitro functional group.

10. The compound as defined by claim 1, wherein the aralkyl radical is selected from the group consisting of benzyl, phenethyl and naphthylen-2-ylmethyl radicals optionally mono- or disubstituted with one or more atoms, groups, functional groups or radicals selected from among a halogen atom, a $CF_3$ radical, an alkyl radical, an alkoxyl radical, a nitro functional group, an alkyl ester group, a carboxyl functional group, a hydroxyl radical, an amino functional group which is optionally substituted with at least one alkyl radical.

11. The compound as defined by claim 1, wherein the heteroaryl radical is selected from the group consisting of pyridyl, furyl, thienyl, isoxazolyl, oxadiazolyl, oxazolyl, imidazolyl, isothiazolyl, quinazolinyl, benzothiadiazolyl, benzimidazolyl, indolyl and benzofuryl radical, optionally substituted with one or more atoms, groups, functional groups or radicals selected from among a halogen atom, a $CF_3$ radical, an alkyl radical, an alkoxyl radical, a nitro functional group, an alkyl ester group, a carboxyl functional group, a hydroxyl radical, an amino functional group which is optionally substituted with at least one alkyl radical.

12. The compound as defined by claim 1, wherein at least one of the following conditions is satisfied:
- X is —N—$R_7$,
- R1 is an alkyl radical or an aryl radical,
- R2 is a hydrogen atom, an alkyl radical, an aryl radical,
- R7 is a hydrogen atom or an alkyl radical,
- m is equal to 0,
- n is equal to 0.

13. The compound as defined by claim 1, selected from the group consisting of:
1. Ethyl(4-{4-[5-(4-tert-butylphenyl)-4-methyl-4H-[1,2,4]-triazol-3-ylsulfanyl]-2-heptyloxybenzylamino}phenyl)acetate;
2. (4-{4-[5-(4-tert-Butylphenyl)-4-methyl-4H-[1,2,4]-triazol-3-ylsulfanyl]-2-heptyloxybenzylamino }phenyl)acetic acid;
3a. (4-{4-[5-(4-tert-Butylphenyl)-4-methyl-4H-[1,2,4]-triazol-3-ylsulfanyl]-2-phenethyloxybenzylamino} phenyl)acetic acid;
3b. Ethyl(4-{4-[5-(4-tert-butylphenyl)-4-methyl-4H-[1,2,4]-triazol-3-ylsulfanyl]-2-phenethyloxy benzylamino}phenyl)acetate;

4a. (4-{4-[5-(4-tert-Butylphenyl)-4-methyl-4H-[1,2,4]-triazol-3-ylsulfanyl]-2-benzyloxybenzylamino}phenyl)acetic acid;

4b. Ethyl(4-{4-[5-(4-tert-butylphenyl)-4-methyl-4H-[1,2,4]-triazol-3-ylsulfanyl]-2-benzyloxybenzylamino}phenyl)acetate;

5a. (4-{4-[5-(4-tert-Butylphenyl)-4-methyl-4H-[1,2,4]-triazol-3-ylsulfanyl]-2-propoxybenzylamino}phenyl)acetic acid;

5b. Ethyl(4-{4-[5-(4-tert-butylphenyl)-4-methyl-4H-[1,2,4]-triazol-3-ylsulfanyl]-2-propoxybenzylamino}phenyl)acetate;

6a. {4-[4-(4-Methyl-4H-[1,2,4]-triazol-3-ylsulfanyl)-2-heptyloxybenzylamino]phenyl}acetic acid;

6b. Ethyl {4-[4-(4-methyl-4H-[1,2,4]-triazol-3-ylsulfanyl)-2-heptyloxybenzylamino]phenyl}acetate;

7a. {4-[4-(4-Methyl-4H-[1,2,4]-triazol-3-ylsulfanyl)-2-phenethyloxybenzylamino]phenyl}acetic acid;

7b. Ethyl {4-[4-(4-methyl-4H-[1,2,4]-triazol-3-ylsulfanyl)-2-phenethyloxybenzyl amino]phenyl}acetate;

8a. {4-[4-(4-Methyl-4H-[1,2,4]-triazol-3-ylsulfanyl)-2-benzyloxybenzylamino]phenyl}acetic acid;

8b. Ethyl {4-[4-(4-methyl-4H-[1,2,4]-triazol-3-ylsulfanyl)-2-benzyloxybenzylamino]phenyl}acetate;

9a. {4-[4-(4-Methyl-4H-[1,2,4]-triazol-3-ylsulfanyl)-2-propoxybenzylamino]phenyl}acetic acid;

9b. Ethyl {4-[4-(4-methyl-4H-[1,2,4]-triazol-3-ylsulfanyl)-2-propoxybenzylamino]phenyl}acetate;

10a. (4-{4-[5-(4,5-Dichloroimidazol-1-ylmethyl)-4-methyl-4H-[1,2,4]-triazol-3-ylsulfanyl]-2-heptyloxybenzylamino}phenyl)acetic acid;

10b. Ethyl(4-{4-[5-(4,5-dichloroimidazol-1-ylmethyl)-4-methyl-4H-[1,2,4]-triazol-3-ylsulfanyl]-2-heptyloxybenzylamino}phenyl)acetate;

11a. (4-{4-[5-(4,5-Dichloroimidazol-1-ylmethyl)-4-methyl-4H-[1,2,4]-triazol-3-ylsulfanyl]-2-phenethyloxybenzylamino}phenyl)acetic acid;

11b. Ethyl(4-{4-[5-(4,5-dichloroimidazol-1-ylmethyl)-4-methyl-4H-[1,2,4]-triazol-3-ylsulfanyl]-2-phenethyloxybenzylamino}phenyl)acetate;

12a. (4-{4-[5-(4,5-Dichloroimidazol-1-ylmethyl)-4-methyl-4H-[1,2,4]-triazol-3-ylsulfanyl]-2-benzyloxybenzylamino}phenyl)acetic acid;

12b. Ethyl(4-{4-[5-(4,5-dichloroimidazol-1-ylmethyl)-4-methyl-4H-[1,2,4]-triazol-3-ylsulfanyl]-2-benzyloxybenzylamino}phenyl)acetate;

13a. (4-{4-[5-(4-tert-Butylphenyl)-4-(4-chlorophenyl)-4H-[1,2,4]-triazol-3-ylsulfanyl]-2-benzyloxybenzylamino}phenyl)acetic acid;

13b. Ethyl(4-{4-[5-(4-tert-butylphenyl)-4-(4-chlorophenyl)-4H-[1,2,4]-triazol-3-ylsulfanyl]-2-benzyloxybenzylamino}phenyl)acetate;

14a. (4-{4-[5-(4-tert-Butylphenyl)-4-(4-chlorophenyl)-4H-[1,2,4]-triazol-3-ylsulfanyl]-2-phenethyloxybenzylamino}phenyl)acetic acid;

14b. Ethyl(4-{4-[5-(4-tert-butylphenyl)-4-(4-chlorophenyl)-4H-[1,2,4]-triazol-3-ylsulfanyl]-2-phenethyloxybenzylamino}phenyl)acetate;

15a. (4-{4-[5-(4-tert-Butylphenyl)-4-(4-chlorophenyl)-4H-[1,2,4]-triazol-3-ylsulfanyl]-2-propoxybenzylamino}phenyl)acetic acid;

15b. Ethyl(4-{4-[5-(4-tert-butylphenyl)-4-(4-chloro phenyl)-4H-[1,2,4]-triazol-3-ylsulfanyl]-2-propoxybenzylamino}phenyl)acetate;

16a. {4-[4-(4-Methyl-5-thiophen-3-ylmethyl-4H-[1,2,4]-triazol-3-ylsulfanyl)-2-heptyloxylbenzylamino]phenyl}acetic acid;

16b. Ethyl {4-[4-(4-methyl-5-thiophen-3-ylmethyl-4H-[1,2,4]-triazol-3-ylsulfanyl)-2-heptyloxy benzylamino]phenyl}acetate;

17a. {4-[4-(4-Methyl-5-thiophen-3-ylmethyl-4H-[1,2,4]-triazol-3-ylsulfanyl)-2-benzyloxybenzylamino]phenyl}acetic acid;

17b. Ethyl {4-[4-(4-methyl-5-thiophen-3-ylmethyl-4H-[1,2,4]-triazol-3-ylsulfanyl)-2-benzyloxybenzyl amino]phenyl}acetate;

18a. {4-[4-(4-Methyl-5-thiophen-3-ylmethyl-4H-[1,2,4]-triazol-3-ylsulfanyl)-2-phenethyloxybenzylamino]phenyl}acetic acid;

18b. Ethyl {4-[4-(4-methyl-5-thiophen-3-ylmethyl-4H-[1,2,4]-triazol-3-ylsulfanyl)-2-phenethyloxybenzyl amino]phenyl}acetate;

19a. {4-[4-(4-Methyl-5-thiophen-3-ylmethyl-4H-[1,2,4]-triazol-3-ylsulfanyl)-2-propoxybenzylamino]phenyl}acetic acid;

19b. Ethyl {4-[4-(4-methyl-5-thiophen-3-ylmethyl-4H-[1,2,4]-triazol-3-ylsulfanyl)-2-propoxybenzylamino]phenyl}acetate;

20a. (4-{4-[5-(7-Methylindan-4-yloxymethyl)-4-phenyl-4H-[1,2,4]-triazol-3-ylsulfanyl]-2-heptyloxybenzyl amino}phenyl)acetic acid;

20b. Ethyl(4-{4-[5-(7-methylindan-4-yloxymethyl)-4-phenyl-4H-[1,2,4]-triazol-3-ylsulfanyl]-2-heptyloxybenzyl amino}phenyl)acetate;

21a. (4-{4-[5-(7-Methylindan-4-yloxymethyl)-4-phenyl-4H-[1,2,4]-triazol-3-ylsulfanyl]-2-benzyloxybenzyl amino}phenyl)acetic acid;

21b. Ethyl(4-{4-[5-(7-methylindan-4-yloxymethyl)-4-phenyl-4H-[1,2,4]-triazol-3-ylsulfanyl]-2-benzyloxybenzyl amino}phenyl)acetate;

22a. (4-{4-[5-(7-Methylindan-4-yloxymethyl)-4-phenyl-4H-[1,2,4]-triazol-3-ylsulfanyl]-2-phenethyloxybenzyl amino}phenyl)acetic acid;

22b. Ethyl(4-{4-[5-(7-methylindan-4-yloxymethyl)-4-phenyl-4H-[1,2,4]-triazol-3-ylsulfanyl]-2-phenethyloxybenzyl amino}phenyl)acetate;

23a. (4-{4-[5-(7-Methylindan-4-yloxymethyl)-4-phenyl-4H-[1,2,4]-triazol-3-ylsulfanyl]-2-propoxybenzyl amino}phenyl)acetic acid;

23b. Ethyl(4-{4-[5-(7-methylindan-4-yloxymethyl)-4-phenyl-4H-[1,2,4]-triazol-3-ylsulfanyl]-2-propoxybenzyl amino}phenyl)acetate;

24. Methyl(4-{4-[5-(4-tert-butylphenyl)-4-methyl-4H-[1,2,4]-triazol-3-ylsulfanyl]-2-heptyloxybenzylamino}phenyl)acetate;

25. 2-(4-{4-[5-(4-tert-Butylphenyl)-4-methyl-4H-[1,2,4]-triazol-3-ylsulfanyl]-2-heptyloxybenzylamino}phenyl)-N-hexylacetamide;

26. 2-(4-{4-[5-(4-tert-Butylphenyl)-4-methyl-4H-[1,2,4]-triazol-3-ylsulfanyl]-2-heptyloxy benzylamino}phenyl)-1-morpholin-4-ylethanone;

27. 2-(4-{4-[5-(4-tert-Butylphenyl)-4-methyl-4H-[1,2,4]-triazol-3-ylsulfanyl]-2-heptyloxybenzylamino}phenylacetamide;

28. 2-(4-{4-[5-(4-tert-Butylphenyl)-4-methyl-4H-[1,2,4]-triazol-3-ylsulfanyl]-2-heptyloxybenzylamino}phenyl)-N-ethylacetamide;

29. {4-[4-(5-Heptyl-4-methyl-4H-[1,2,4]-triazol-3-ylsulfanyl)-2-heptyloxybenzyloxy]phenyl}acetic acid methyl ester;

30. {4-[2-Heptyloxy-4-(5-hexyl-4-methyl-4H-[1,2,4]-triazol-3-ylsulfanyl) benzyloxy]phenyl}acetic acid;

31. {4-[4-(5-Heptyl-4-methyl-4H-[1,2,4]-triazol-3-ylsulfanyl)-2-propoxybenzylamino ]phenyl}acetic acid ethyl ester;
32. 4-[2-Propoxy-4-(5-pyridin-4-yl-4H-[1,2,4]-triazol-3-ylsulfanyl) benzylamino]phenyl}acetic acid ethyl ester;
33. {4-[4-(4-Methyl-5-pyridin-4-yl-4H-[1,2,4]-triazol-3-ylsulfanyl)-2-propoxybenzylamino ]phenyl}acetic acid ethyl ester;
34. {4-[4-(5-Heptyl-4-methyl-4H-[1,2,4]-triazol-3-ylsulfanyl)-2-propoxybenzylamino ]phenyl}acetic acid;
35. {4-[2-Propoxy-4-(5-pyridin-4-yl-4H-[1,2,4]-triazol-3-ylsulfanyl) benzylamino]phenyl}acetic acid;
36. {4-[4-(4-Methyl-5-pyridin-4-yl-4H-[1,2,4]-triazol-3-ylsulfanyl)-2-propoxybenzylamino ]phenyl}acetic acid;
37. Butyl(4-{4-[5-(4-tert-butylphenyl)-4-methyl-4H-[1,2,4]-triazol-3-ylsulfanyl)-2-heptyloxybenzyl amino}phenyl)acetate;
38. Octyl(4-{4-[5-(4-tert-butylphenyl)-4-methyl-4H-[1,2,4]-triazol-3-ylsulfanyl)-2-heptyloxybenzyl amino}phenyl)acetate;
39. Nonyl(4-{4-[5-(4-tert-butylphenyl)-4-methyl-4H-[1,2,4]-triazol-3-ylsulfanyl)-2-heptyloxybenzyl amino}phenyl)acetate;
40. 2-(4-{4-[5-(4-tert-Butylphenyl)-4-methyl-4H-[1,2,4]-triazol-3-ylsulfanyl)-2-heptyloxybenzyl amino}phenyl)-N-methylacetamide;
41. 2-(4-{4-[5-(4-tert-Butylphenyl)-4-methyl-4H-[1,2,4]-triazol-3-ylsulfanyl)-2-heptyloxybenzyl amino}phenyl)-N-ethylacetamide;
42. 2-(4-{4-[5-(4-tert-Butylphenyl)-4-methyl-4H-[1,2,4]-triazol-3-ylsulfanyl)-2-heptyloxybenzyl amino}phenyl)-N-pentylacetamide;
43. 2-(4-{4-[5-(4-tert-Butylphenyl)-4-methyl-4H-[1,2,4]-triazol-3-ylsulfanyl)-2-heptyloxybenzyl amino}phenyl)-N-heptylacetamide;
44. (4-{4-[5-(4-tert-Butylphenyl)-4-methyl-4H-[1,2,4]-triazol-3-ylsulfanyl)-2-heptyloxybenzyloxy }phenyl) acetic acid;
45. Methyl(4-{4-[5-(4-tert-butylphenyl)-4-methyl-4H-[1,2,4]-triazol-3-ylsulfanyl )-2-heptyloxybenzyl oxy}phenyl)acetate;
46. Methyl(4-{4-[5-(4-tert-butylphenyl)-4-methyl-4H-[1,2,4]-triazol-3-ylsulfanyl )-2-heptyloxybenzyl sulfanyl}phenyl)acetate;
47. (4-{4-[5-(4-tert-Butylphenyl)-4-methyl-4H-[1,2,4]-triazol-3-ylsulfanyl)-2-heptyloxybenzyl sulfanyl}phenyl)acetic acid; and
48. 2-(4-{4-[5-(4-tert-Butylphenyl)-4-methyl-4H-[1,2,4]-triazol-3-ylsulfanyl]-2-heptyloxybenzylamino }phenyl)-N-octylacetamide.

14. A composition, comprising at least one compound as defined by claim 1 and a physiologically acceptable carrier therefor.

15. The composition as defined by claim 14, said at least one compound comprising from 0.001% to 10% by weight thereof.

16. The composition as defined by claim 14, said at least one compound comprising from 0.01% to 1% by weight thereof.

17. The composition as defined by claim 14, said at least one compound comprising from 0.001% to 3% by weight thereof.

* * * * *